(12) United States Patent
Mann et al.

(10) Patent No.: US 9,476,098 B2
(45) Date of Patent: Oct. 25, 2016

(54) MULTIGENE PROGNOSTIC ASSAY FOR LUNG CANCER

(75) Inventors: Michael J. Mann, San Francisco, CA (US); David M. Jablons, San Francisco, CA (US); Johannes Kratz, Cambridge, MA (US); David M. Berryman, Foster City, CA (US)

(73) Assignees: The Regents of the University of California, Oakland, CA (US); Encore Clinical, Inc., Los Altos, CA (US)

( * ) Notice: Subject to any disclaimer, the term of this patent is extended or adjusted under 35 U.S.C. 154(b) by 388 days.

(21) Appl. No.: 13/539,278

(22) Filed: Jun. 29, 2012

(65) Prior Publication Data

US 2013/0059747 A1 Mar. 7, 2013

Related U.S. Application Data

(60) Provisional application No. 61/504,063, filed on Jul. 1, 2011, provisional application No. 61/504,193, filed on Jul. 2, 2011.

(51) Int. Cl.
| | |
|---|---|
| *C40B 30/04* | (2006.01) |
| *C12Q 1/68* | (2006.01) |
| *G01N 33/574* | (2006.01) |

(52) U.S. Cl.
CPC ....... *C12Q 1/6886* (2013.01); *G01N 33/57423* (2013.01); *C12Q 2600/118* (2013.01); *C12Q 2600/158* (2013.01); *G01N 2800/52* (2013.01)

(58) Field of Classification Search
CPC .......... C12Q 1/6886; C12Q 2600/118; C12Q 2600/158
USPC ........................................ 435/6.1, 6.14, 7.1
See application file for complete search history.

(56) References Cited

U.S. PATENT DOCUMENTS

| | | | |
|---|---|---|---|
| 6,019,944 A | 2/2000 | Buechler | |
| 2006/0211036 A1 | 9/2006 | Chou et al. | |
| 2013/0123130 A1 | 5/2013 | Jablons et al. | |

FOREIGN PATENT DOCUMENTS

| | | |
|---|---|---|
| CN | 101821405 A | 9/2010 |
| CN | 102099484 A | 6/2011 |
| WO | WO-2008/151072 A1 | 12/2008 |
| WO | WO-2011/109440 A1 | 9/2011 |
| WO | WO-2013/006503 A1 | 1/2013 |

OTHER PUBLICATIONS

Arvidsson et al.; QuantPrime—a flexible tool for reliable high-throughput primer design for quantitative PCR; BMC Bioinformatics; 9:465; pp. 1-15; published Nov. 1, 2008.*

Bao, J.J. (Oct. 10, 1997). "Capillary Electrophoretic Immunoassays," *J. Chromatogr. B. Biomed. Sci.* 699(1-2):463-80.

Batzer, M.A. et al. (Sep. 25, 1991). "Enhanced Evolutionary PCR Using Oligonucleotides With Inosine at the 3'-Terminus," *Nucleic Acid Res.* 19(18):5081.

Chee, M. et al. (Oct. 25, 1996). "Accessing Genetic Information with High-Density DNA Arrays," *Science* 274(5287):610-614.

Chen, H. et al. (Jan. 4, 2007). "A Five-Gene Signature and Clinical Outcome in Non-Small-Cell Lung Cancer," *The New England Journal of Medicine* 356(1):11-20.

Drmanac, S. et al. (Jan. 1998). "Accurate Sequencing by Hybridization for DNA Diagnostics and Individual Genomics," *Nat. Biotechnol.* 16(1):54-58.

Drmanac, R. et al. (Jun. 11, 1993). "DNA Sequence Determination by Hybridization: A Strategy for Efficient Large-Scale Sequencing," *Science* 260(5114):1649-1652.

Fink, P.C. et al. (Apr. 1989). "Measurement of Proteins with the Behring Nephelometer. A Multicentre Evaluation," *J. Clin. Chem. Clin. Biochem.* 27(4):261-276.

Fu, D.J. et al. (Apr. 1998). "Sequencing Exons 5 to 8 of the p53 Gene by MALDI-TOF Mass Spectrometry," *Nat. Biotechnol.* 16(4):381-384.

International Search Report mailed on Sep. 27, 2012, for PCT Patent Application No. PCT/US2012/045139, filed on Jun. 29, 2012, six pages.

McCafferty, J. et al. (Dec. 6, 1990). "Phage Antibodies: Filamentous Phage Displaying Antibody Variable Domains," *Nature* 348(6301):552-554.

Ng, J.H. et al. (Jul.-Sep. 2002). "Biomedical Applications of Protein Chips," *J. Cell Mol. Med.* 6(3):329-340.

Ohtsuka, E. et al. (Mar. 10, 1985). "An Alternative Approach to Deoxyoligonucleotides as Hybridization Probes by Insertion of Deoxyinosine at Ambiguous Codon Positions," *J. Biol. Chem.* 260(5)2605-2608.

Rongen, H.A.H. et al. (May 26, 1997). "Liposomes and Immunoassays," *J. Immunol. Methods*, 204(2):105-133.

Rossolini, G.M. et al. (Apr. 1994). "Use of Deoxyinosine-Containing Primers vs Degenerate Primers for Polymerase Chain Reaction Based on Ambiguous Sequence Information," *Mol. Cell. Probes* 8(2):91-98.

Schmalzing, D. et al. (Nov. 1997). "Capillary Electrophoresis Based Immunoassays: A Critical Review," *Electrophoresis*, 18(12-13):2184-2193.

Sears, L.E. et al. (Oct. 1992). "CircumVent Thermal Cycle Sequencing and Alternative Manual and Automated DNA Sequencing Protocols Using the Highly Thermostable Vent$_R$™ (exo-) DNA Polymerase," *Biotechniques* 13(4):626-633.

(Continued)

*Primary Examiner* — Antonio Galisteo Gonzalez
(74) *Attorney, Agent, or Firm* — Morrison & Foerster LLP

(57) ABSTRACT

The present invention provides methods for providing a prognosis for lung cancer using a panel of eleven molecular markers that includes BAG1, BRCA1, CDC6, CDK2AP1, ERBB3, FUT3, IL11, LCK, RND3, SH3BGR, and WNT3A, which are differentially expressed in lung cancer. The eleven markers are related to patient prognosis to 5-year overall survival outcomes, and are particularly useful in providing a prognosis for non-squamous NSCLC.

35 Claims, 12 Drawing Sheets

(56) References Cited

OTHER PUBLICATIONS

Self, C.H. et al. (Feb. 1996). "Advances in Immunoassay Technology," *Curr. Opin. Biotechnol.* 7(1):60-65.
Written Opinion of the International Searching Authority mailed on Sep. 27, 2012, for PCT Patent Application No. PCT/US2012/045139, filed on Jun. 29, 2012, ten pages.
Zimmermann, J. et al. (1992). "Fully Automated Sanger Sequencing Protocol for Double Stranded DNA," *Methods Mol. Cell Biol.* 3:39-42.
Kratz J.R. et al. (2012). "A practical molecular assay to predict survival in resected non-squamous, non-small-cell lung cancer: development and International validation studies," and supplementary webappendix *Lancet* 379:823-32 (18 pages).
Glazer, C.A. et al., (2009) "Integrative Discovery of Epigenetically Depressed Cancer Testis Antigens in NSCLC" PLoS One vol. 4, No. 12, e8189.
Kratz J.R. et al. (2009). "Genomic Prognostic Models in Early Stage Lung Cancer" Clinical Lung Cancer 10(3): 151-157. (PDF retrieved from http://www.medscape.com/viewarticle/705730_print, p. 1-7 on Mar. 10, 2016).
Pisters, K. M.W. (Dec. 1, 2007) "Cancer Care Ontario and American Society of Clinical Oncology Adjuvant Chemotherapy and Adjuvant Radiation Therapy for Stages I-IIIA Resectable Non-Small-Cell Lung Cancer Guideline" *Journal of Clinical Oncology* vol. 25 34:5506-5518.

\* cited by examiner

| Gene name | Chromosome | Reference sequence | Protein location | Relevant biological functions and pathways | Role in algorithm |
|---|---|---|---|---|---|
| BAG1 | 9p12 | NM_004323 | Cytoplasm | Apoptosis; cell surface receptor linked signalling | Prognosis |
| BRCA1 | 17q21-q24 | NM_007294 | Nucleus | Induction of apoptosis; protein ubiquitination; regulation of G2/M transition DNA damage checkpoints; regulation of DNA repair | Prognosis |
| CDC6 | 17q21.3 | NM_001254 | Nucleus | Regulation of transcription involved in G1/S phase of mitotic cell cycle; regulation of cell proliferation | Prognosis |
| CDC2AP1 | 12q24 | NM_004642 | Nucleus | Regulation of S phase of mitotic cell cycle; DNA-dependent DNA replication | Prognosis |
| EPHB2 | 1p13 | NM_001982 | Plasma membrane | Regulation of cell adhesion; transmembrane receptor protein tyrosine kinase signalling; regulation of phosphoinositide 3-kinase cascade; regulation of cell proliferation | Prognosis |
| FUT3 | 19p13.3 | NM_000149 | Cytoplasm | Carbohydrate metabolism; protein amino acid glycosylation | Prognosis |
| IL11 | 19q13.3-q13.4 | NM_000641 | Extracellular | Regulation of cell proliferation; B-cell differentiation; megakaryocyte differentiation; regulation of peptidyl-serine phosphorylation; regulation of MAPKK cascade | Prognosis |
| LCK | 1p34.3 | NM_001042771 | Cytoplasm | Induction of apoptosis; activation of caspase activity; regulation of T-cell receptor signalling; lymphocyte migration | Prognosis |
| RND3 | 2q23.3 | NM_005168 | Cytoplasm | Cell adhesion; small GTPase mediated signal transduction; actin cytoskeleton organization | Prognosis |
| SH3BGR | 21q22.3 | NM_007341 | Cytoplasm | Protein complex assembly | Prognosis |
| WNT3A | 1q42 | NM_033131 | Extracellular | Canonical Wnt receptor signalling; multicellular organismal development; regulation of cell proliferation and differentiation; regulation of catenin protein nuclear translocation | Prognosis |
| ESD | 13q14.1-q14.2 | NM_001984 | Cytoplasm | Recycling of sialic acids; serine hydrolysis | Reference |
| TBP | 6q27 | NM_003194 | Nucleus | Transcription initiation from RNA polymerase II promoter; RNA elongation from RNA polymerase II promoter; transcription from RNA polymerase III promoter | Reference |
| YAP1 | 11q13 | NM_006106 | Nucleus | Hippo signalling cascade; regulation of transcription; contact inhibition | Reference |

Figure 4

MULTIGENE PROGNOSTIC ASSAY FOR LUNG CANCER

CROSS-REFERENCE TO RELATED APPLICATIONS

This application claims the benefit of U.S. Provisional Patent Application Ser. No. 61/504,063, filed Jul. 1, 2011, and U.S. Provisional Patent Application Ser. No. 61/504,193, filed Jul. 2, 2011, both of which are incorporated herein by reference in their entireties.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The likelihood of long-term survival for patients with lung cancer is poorly defined by clinical stage and histopathological findings. Microarray identification of genes identified as prognostic for lung cancer have been published, although there exists a need for an accurate multigene quantitative polymerase chain reaction (PCR) assay that can predict risk of mortality among patients with lung cancer.

BRIEF SUMMARY OF THE INVENTION

In one aspect, a method of providing a prognosis for lung cancer in a subject is provided, the method comprising the steps of: (a) contacting a biological sample from the subject with reagents that specifically bind to a panel of biomarkers comprising BAG1, BRCA1, CDC6, CDK2AP1, ERBB3, FUT3, IL11, LCK, RND3, SH3BGR, and WNT3, and (b) determining whether or not the markers are differentially expressed in the sample; thereby providing a prognosis for lung cancer.

In one embodiment, the reagent is a nucleic acid. In another embodiment, the reagent is an oligonucleotide. In another embodiment, the reagent is a PCR primer set. In another embodiment, the reagent is an antibody.

In one embodiment, the lung cancer is non-squamous cell lung cancer. In another embodiment, the non-squamous cell lung cancer is stage I. In another embodiment, the non-squamous cell lung cancer is stage II. In another embodiment, the non-squamous cell lung cancer is stage III. In another embodiment, the non-squamous cell lung cancer is stage IV.

In one embodiment, the sample is from lung tissue or a lung tumor biopsy.

In one embodiment, the prognosis provides a risk assessment. In some embodiments, the risk assessment is based on 5-year mortality. In some embodiments the risk assessment is a high, intermediate, or low risk assessment for 5-year mortality.

In one aspect, a kit is provided, the kit comprising reagents that specifically bind to a panel of biomarkers comprising BAG1, BRCA1, CDC6, CDK2AP1, ERBB3, FUT3, IL11, LCK, RND3, SH3BGR, and WNT3. In one embodiment, the reagent is a reverse transcriptase set.

In yet another aspect, a method of determining the prognosis of a subject having a lung cancer is provided by measuring in a biological sample the methylation levels of a panel of biomarkers comprising BAG1, BRCA1, CDC6, CDK2AP1, ERBB3, FUT3, IL11, LCK, RND3, SH3BGR, and WNT3; wherein said biological sample is derived from said subject and said methylation levels are indicative of said prognosis.

In another aspect, a report is provided, the report comprising a prognosis of a subject having a lung cancer, said prognosis having been determined by quantifying in a biological sample of the subject the expression levels of a panel of biomarkers comprising BAG1, BRCA1, CDC6, CDK2AP1, ERBB3, FUT3, IL11, LCK, RND3, SH3BGR, and WNT3; wherein said expression levels are indicative of said prognosis.

In another aspect, a method of determining a treatment plan is provided, the method comprising the steps of: (a) contacting a biological sample from the subject with reagents that each specifically bind to one member of a panel of biomarkers comprising BAG1, BRCA1, CDC6, CDK2AP1, ERBB3, FUT3, IL11, LCK, RND3, SH3BGR, and WNT3, (b) determining whether or not the markers are differentially expressed in the sample, (c) providing a prognosis for lung cancer, (d) determining a risk assessment for 5-year mortality based on the prognosis for lung cancer, and (e) devising a treatment plan based on the risk assessment.

In another aspect, provided is a method of providing a prognosis for lung cancer in a subject, the method comprising the steps of: (a) contacting a biological sample from the subject with reagents that each specifically bind to one member of a panel of biomarkers consisting of BAG1, BRCA1, CDC6, CDK2AP1, ERBB3, FUT3, IL11, LCK, RND3, SH3BGR, and WNT3A, and (b) determining whether or not the biomarkers are differentially expressed in the sample; thereby providing a prognosis for lung cancer. In some embodiments, the determining of whether or not the biomarkers are differentially expressed in the sample further comprises normalizing the levels of expression of the biomarkers to housekeeping genes selected from the group consisting of ESD, TBP, YAP1, and any combinations thereof. In certain embodiments, the levels of expression of the biomarkers are normalized against the average $C_T$ value of the housekeeping genes. In one embodiment, BAG1, BRCA1, CDC6, CDK2AP1, FUT3, IL11, and RND3 indicate an increased likelihood in mortality of the subject, and wherein ERBB3, LCK, SH3BGR, and WNT3A indicate a decreased likelihood in mortality of the subject.

In one embodiment, the reagents are nucleic acids. In another embodiment, the reagents are oligonucleotides. In another embodiment, the reagents are PCR primer sets. In another embodiment, the reagents are antibodies.

In one embodiment, the lung cancer is non-squamous cell lung cancer. In another embodiment, the non-squamous cell lung cancer is stage I. In another embodiment, the non-squamous cell lung cancer is stage II. In another embodiment, the non-squamous cell lung cancer is stage III. In another embodiment, the non-squamous cell lung cancer is stage IV.

In one embodiment, the sample is from a surgically resected tumor. In another embodiment, the sample is from lung tissue or a lung tumor biopsy.

In one embodiment, the prognosis provides a risk assessment. In some embodiments, the risk assessment is based on 5-year mortality. In some embodiments the risk assessment is a high, intermediate, or low risk assessment for 5-year mortality.

In another aspect, provided is a kit comprising reagents that each specifically bind to one member of a panel of biomarkers consisting of BAG1, BRCA1, CDC6, CDK2AP1, ERBB3, FUT3, IL11, LCK, RND3, SH3BGR, and WNT3A. In certain embodiments, the reagents are reverse transcriptase sets. In some embodiments, the kit further comprises housekeeping genes selected from the group consisting of ESD, TBP, YAP1, and any combination thereof.

In another aspect, provided is a method of providing a prognosis of a subject having a lung cancer, said method comprising measuring in a biological sample the methylation levels of a panel of biomarkers consisting of BAG1, BRCA1, CDC6, CDK2AP1, ERBB3, FUT3, IL11, LCK, RND3, SH3BGR, and WNT3A; wherein said biological sample is derived from said subject and said methylation levels are indicative of said prognosis.

In yet another aspect, provided is a report comprising a prognosis of a subject having a lung cancer, said prognosis having been determined by quantifying in a biological sample of the subject the expression levels of a panel of biomarkers consisting of BAG1, BRCA1, CDC6, CDK2AP1, ERBB3, FUT3, IL11, LCK, RND3, SH3BGR, and WNT3A; wherein said expression levels are indicative of said prognosis. In some embodiments, the quantifying of the subject the expression levels of a panel of biomarkers in the biological sample further comprises normalizing the expression levels of the biomarkers to housekeeping genes selected from the group consisting of ESD, TBP, YAP1, and any combinations thereof. In certain embodiments, the expression levels of the biomarkers are normalized against the average $C_T$ value of the housekeeping genes.

In yet another aspect, provided is a method of determining a treatment plan, the method comprising the steps of: (a) contacting a biological sample from the subject with reagents that each specifically bind to one member of a panel of biomarkers consisting of BAG1, BRCA1, CDC6, CDK2AP1, ERBB3, FUT3, IL11, LCK, RND3, SH3BGR, and WNT3A, (b) determining whether or not the markers are differentially expressed in the sample, (c) providing a prognosis for lung cancer, (d) determining a risk assessment for 5-year mortality based on the prognosis for lung cancer, and (e) devising a treatment plan based on the risk assessment. In some embodiments, the determining of whether or not the biomarkers are differentially expressed in the sample further comprises normalizing the levels of expression of the biomarkers to housekeeping genes selected from the group consisting of ESD, TBP, YAP1, and any combinations thereof. In certain embodiments, the levels of expression of the biomarkers are normalized against the average $C_T$ value of the housekeeping genes.

In yet another aspect, provided is a method of providing a prognosis for lung cancer in a subject, the method comprising the steps of: (a) contacting a biological sample from the subject with reagents that each specifically bind to one member of a panel of biomarkers consisting of BAG1, BRCA1, CDC6, CDK2AP1, ERBB3, FUT3, IL11, LCK, RND3, SH3BGR, and WNT3A; (b) determining a risk score of the subject based on the levels of expression of the biomarkers in the sample; and (c) providing a prognosis for lung cancer based on the risk score of the subject. In some embodiments, the determining of a risk score of the subject based on the levels of expression of the biomarkers in the sample further comprises normalizing the levels of expression of the biomarkers to housekeeping genes selected from the group consisting of ESD, TBP, YAP1, and any combinations thereof. In certain embodiments, the levels of expression of the biomarkers are normalized against the average $C_T$ value of the housekeeping genes.

BRIEF DESCRIPTION OF THE FIGURES

FIG. 4 is a chart summarizing the algorithm genes used in the algorithm in Example 2.

DETAILED DESCRIPTION OF THE INVENTION

Introduction

Figure 1:
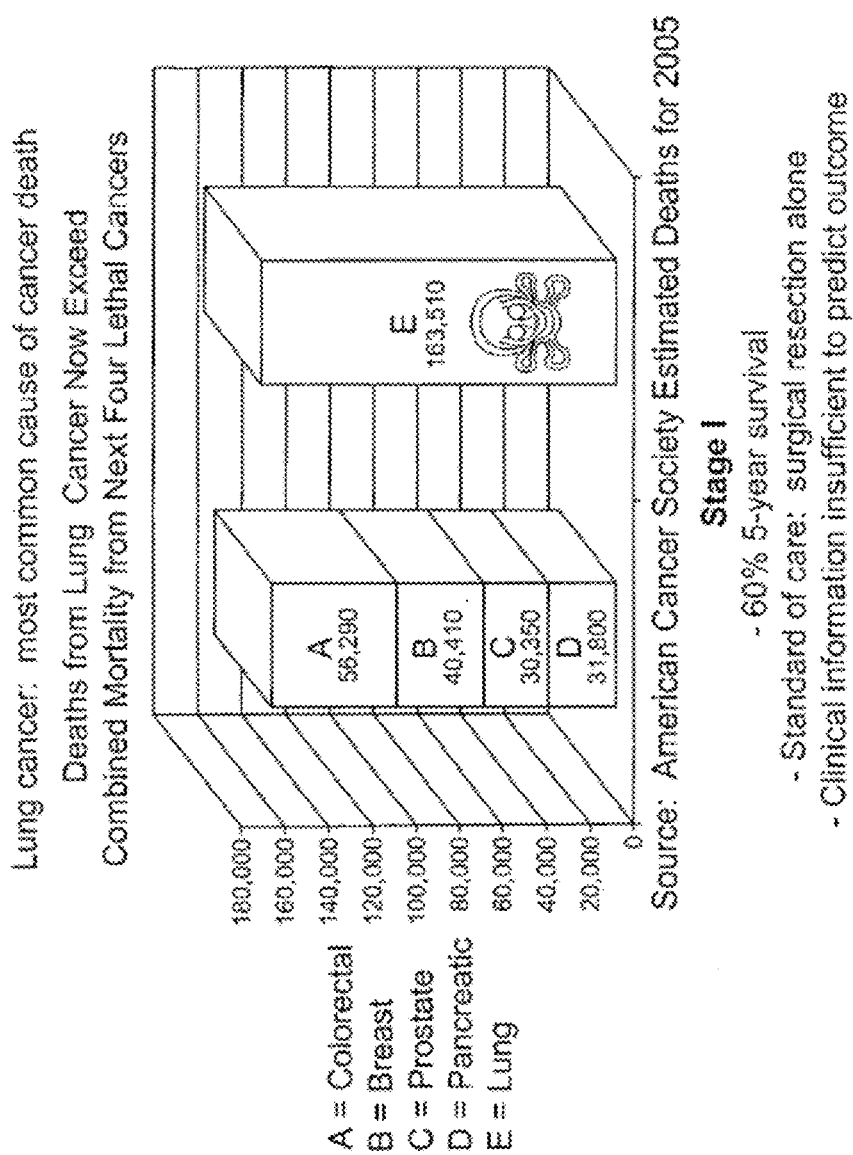
FIG. 1 shows that lung cancer is the most common cause of cancer death and shows that for stage 1 cancers, the prognosis for 5-year survival is approximately 60%.
Figure 2:
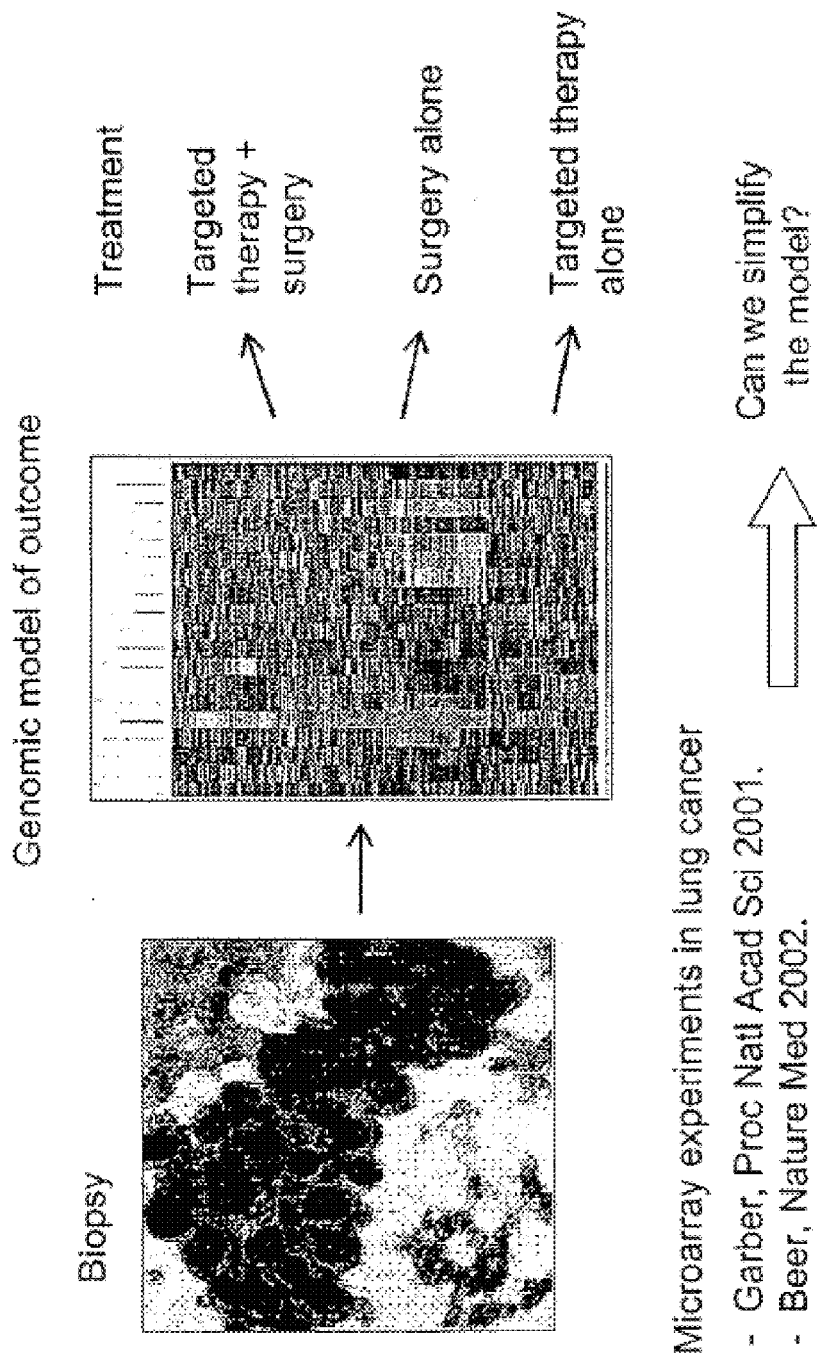
FIG. 2 shows genomic models of prognosis.

The invention features the identification of expression profiles of certain groups of genes which allows accurate prognosis of mortality in early stage lung cancer. Ideally, a prognostic tool should provide accurate risk stratification, should be clinically feasible to employ in day-to-day practice, and should be cost effective. Such an assay would be of particular benefit to patients with surgically resected stage I or II non-squamous NSCLC. The current standard of care for most stage I non-squamous NSCLC is lobectomy and mediastinal lymph node dissection, without adjuvant chemotherapy. Better identification of good prognosis patient subsets might allow lesser surgical procedures to be employed with equal survival potential. Conversely, stage I subsets with a poor prognosis could be selected for treatment with adjuvant chemotherapy to reduce the risk of distant recurrence using current standard-of-care agents. Furthermore, patients identified to have a poor prognosis might also be considered for inclusion into clinical trials testing novel approaches and new therapeutic agents. Considering the current limitations of chemotherapy in stage I disease, a bioassay that is both prognostic and predictive of chemotherapy benefit would be especially beneficial. Lastly, stage I non-squamous NSCLC is likely to be of increasing importance in the future. While approximately 20-30% of patients currently diagnosed with non-squamous NSCLC are stage I, this proportion probably will grow due to the recent advent of lung cancer screening by computerized tomography.

Patients with stage II NSCLC are currently recommended to undergo adjuvant chemotherapy after attempt at curative resection. The documented benefit of chemotherapy for these patients in terms of absolute improvement in 5-year survival, however, is small. As a result, many patients forego chemotherapy, particularly as they recover from their attempt at curative surgery. A bioassay that can better assign risk of recurrence to stage II patients may therefore improve compliance with current standard-of-care recommendations for adjuvant therapy in patients found to be at higher risk of recurrence. In a controlled, experimental setting, therapy may even be withheld from patients found to be at the lowest risk for recurrence even in stage II.

In an embodiment described herein, an assay was developed based on the expression patterns of 426 patients who underwent resection of stage I-IV non-small cell lung cancer (NSCLC) at the University of California, San Francisco. RNA was extracted from FFPE tissues samples and expression levels for 11 target genes related to patient prognosis were assessed. An assay was sought that would tend to assign a higher risk score on average to patients who had died than to those who had survived a 5-year follow-up period. Patients whose samples received higher risk scores would be considered at higher risk of dying within a 5-year period after operation, whereas patients whose samples received a low score would be more likely to have survived during this time interval after their operations.

The prognostic assay was developed by correlating expression patterns of BAG1, BRCA1, CDC6, CDK2AP1, ERBB3, FUT3, IL11, LCK, RND3, SH3BGR, WNT3A, which are related to patient prognosis (particularly as prognosis relates to 5-year overall survival outcomes) using Cox proportional hazards modeling. The prognostic assay provides a prognosis for lung cancer in a subject by determining the expression of BAG1, BRCA1, CDC6, CDK2AP1, ERBB3, FUT3, IL11, LCK, RND3, SH3BGR, and WNT3A in a sample. The selection of each of a panel of biomarkers that includes BAG1, BRCA1, CDC6, CDK2AP1, ERBB3, FUT3, IL11, LCK, RND3, SH3BGR, and WNT3A offer a vast improvement over the prior art.

A risk score for each patient is then derived by inserting the expression levels of each of the 11 prognostic genes into a risk score algorithm. Risk groups are also described herein based on these risk scores by placing patients into different risk categories according to their risk score. For example, "Low Risk," "Intermediate Risk," or "High Risk."

Further described herein is a multigene diagnostic kit, composed of the markers described herein that can be used to provide a prognosis for lung cancer patients, and a report comprising a prognosis of a subject having lung cancer by quantifying the expression levers of the markers described herein.

Definitions

"Lung cancer" refers generally to two main types of lung cancer categorized by the size and appearance of the malignant cells: non-small cell (approximately 80% of cases) and small-cell (roughly 20% of cases) lung cancer. "Non-small cell lung cancer" (NSCLC) includes squamous cell carcinoma. Lung adenocarcinoma is the most common subtype of NSCLC, and other subtypes of lung cancer include bronchioloalveolar carcinoma, large cell carcinoma, carcinoid, adenoid cystic carcinoma, cylindroma, and mucoepidermoid carcinoma. In one embodiment, lung cancers are staged according to stages I-IV, with I being an early stage and IV being the most advanced.

"Prognosis" refers, e.g., to overall survival, long term mortality, and disease free survival. In one embodiment, long term mortality refers to death within 5 years after diagnosis of lung cancer.

"Risk assessment" refers to the relative risk an individual faces with respect to mortality. For example, a prognosis providing a high risk assessment for 5-year mortality has a greater likelihood of mortality within 5 years than an individual having a low risk assessment for 5-year mortality. In one embodiment, the prognosis for long term mortality is "high risk," e.g., high risk of mortality, "intermediate risk," e.g., intermediate risk of mortality, or "low risk," e.g., low risk of mortality. The stage of cancer and the prognosis may be used to tailor a patient's therapy to provide a better outcome, e.g., systemic therapy and surgery, surgery alone, or systemic therapy alone. Risk assessment can be divided as desired, e.g., at the median, in tertiary groups, quaternary groups, and so on.

Other forms of cancer include carcinomas, sarcomas, adenocarcinomas, lymphomas, leukemias, etc., including solid and lymphoid cancers, head and neck cancer, e.g., oral cavity, pharyngeal and tongue cancer, kidney, breast, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma.

The term "marker" refers to a molecule (typically protein, nucleic acid, carbohydrate, or lipid) that is expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, such markers are molecules that are overexpressed in a lung cancer or other cancer cell in comparison to a non-cancer cell, for instance, 1-fold overexpression, 2-fold overexpression, 3-fold overexpression or more in comparison to a normal cell. Further, a marker can be a molecule that is inappropriately synthesized in the cancer cell, for instance, a molecule that contains deletions, additions or mutations in comparison to the molecule expressed on a normal cell. Alternatively, such biomarkers are molecules that are underexpressed in a cancer cell in comparison to a non-cancer cell, for instance, 1-fold underexpression, 2-fold underexpression, 3-fold underexpression, or more. Further, a marker can be a molecule that is inappropriately synthesized in cancer, for instance, a molecule that contains deletions, additions or mutations in comparison to the molecule expressed on a normal cell.

It will be understood by the skilled artisan that markers may be used in combination with other markers or tests for any of the uses, e.g., prediction, diagnosis, or prognosis of cancer, disclosed herein.

"Biological sample" includes sections of tissues such as biopsy and autopsy samples, and frozen sections taken for histologic purposes. Such samples include blood and blood fractions or products (e.g., serum, platelets, red blood cells, and the like), sputum, bronchoalveolar lavage, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue from within the tumor. A diagnosis or prognosis made by endoscopy or radiographic guidance can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "overexpress," "overexpression," or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "underexpress," "underexpression," or "underexpressed" or "downregulated" interchangeably refer to a protein or nucleic acid that is translated or transcribed at a detectably lower level in a cancer cell, in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient compared to a sample of non-cancerous tissue in the context of the present invention.

"Therapeutic treatment" and "cancer therapies" refers to chemotherapy, hormonal therapy, radiotherapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'2 dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing cancer biomarkers in vitro, in cells, or cell extracts, applying putative modulator compounds, and then determining the functional effects on activity, as described above.

Samples or assays comprising cancer biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100% Inhibition of cancer biomarkers is achieved when the activity value relative to the control is about 80%, preferably 50%, more preferably 25-0%. Activation of cancer biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Prognostic Methods

The present invention provides methods of predicting or providing prognosis for lung cancer by detecting the expression of a panel of markers differentially expressed in the cancer. The panel includes the genes that encode BAG1, BRCA1, CDC6, CDK2AP1, ERBB3, FUT3, IL11, LCK, RND3, SH3BGR, and WNT3A. Prediction and prognosis involve determining the level of a panel of lung cancer biomarker polynucleotide or the corresponding polypeptides in a patient or patient sample and then comparing the level to a baseline or range. Typically, the baseline value is representative of levels of the polynucleotide or nucleic acid in a healthy person not suffering from, or destined to develop, lung cancer, as measured using a biological sample such as a lung biopsy or a sample of a bodily fluid. Variation of levels of a polynucleotide or corresponding polypeptides of the invention from the baseline range (either up or down) indicates that the patient has an increased risk of long term mortality.

The algorithm used to calculate a risk assessment score in a method disclosed herein may group the expression level values of genes, and the risk score can be derived from any algorithm known in the art. The Examples provided herein employ exemplary algorithms that can be used to develop a risk assessment. The algorithms are sets of rules for describing the risk assessment of lung cancer using expression of the panel of genes described herein. The rule set may be defined exclusively algebraically but may also include alternative or multiple decision points requiring domain-specific knowledge, expert interpretation or other clinical indicators. Many algorithms that can provide different risk assessments can be developed using expression profiles of the panel of genes described herein. For example, the risk scores of an individual may be generated using a Cox proportional hazard model. An individual's prognostic categorization can also be determined by using a statistical model or a machine learning algorithm, which computes the probability of recurrence based on the individual's gene expression profiles.

Based on the determination of a risk, individuals can be partitioned into risk groups (e.g., tertiles or quartiles) based on a selected value of the risk score, where all individuals with values in a given range can be classified as belonging to a particular risk group. Thus, the values chosen will define risk groups of patients with respectively greater or lesser risk. Risk groups can further be classified on different ranges of mortality, for example, on 6 month, 1-year, 2-year, 3-year, 4-year, 5-year, 10-year, 25-year mortality. Risk groups can further be classified on different ranges of events associated with lung cancer, which can include, but is not limited, likelihood of metastasis, recurrence, etc.

Various technological approaches for determination of expression levels of the panel of genes are set forth herein, including, but not limited to, RT-PCR, microarrays, high-throughput sequencing, serial analysis of gene expression (SAGE) and Digital Gene Expression (DGE). The expression level of each gene may be determined in relation to various features of the expression products of the gene including exons, introns, protein epitopes and protein activity.

In a preferred embodiment, real time or quantitative reverse transcription PCR (RTPCR) is used to examine expression of the eleven biomarkers in the panel using RNA from a biological sample such as tumor tissue. No microdissection is required. RNA extraction can be performed by any method know to those of skill in the art, e.g., methods involving proteinase K tissue digestion and alcohol-based nucleic acid precipitation, treatment with DNAse to digest contaminating DNA, RNA purification using silica-gel-membrane technology, methods utilizing commercially available kits such as Trizol and RNeasy, or any combination thereof. Real time RT-PCR can be performed by any method known to those of skill in the art, e.g., Taqman real time PCR using Applied Biosystem assays. Gene expression is calculated relative to pooled normal lung RNA, and expression is normalized to housekeeping genes. Suitable oligonucleotide primers are selected by those of skill in the art. In one embodiment, the assay is used for stage I, stage II, stage III, or stage IV cancers. In one embodiment, the tissue sample is from a surgically resected tumor.

In one embodiment, RNA biomarkers are examined using nucleic acid binding molecules such as probes, oligonucleotides, oligonucleotide arrays, and primers to detect differential RNA expression in patient samples. In one embodiment, RT-PCR is used according to standard methods known in the art. In another embodiment, quantitative RT-PCR assays such as those utilizing Taqman® assays available from, e.g., Applied Biosystems, can be used to detect nucleic acids and variants thereof. In other embodiments, nucleic acid microarrays can be used to detect nucleic acids Analysis of nucleic acids can be achieved using routine techniques such as Northern analysis, or any other methods based on hybridization to a nucleic acid sequence that is complementary to a portion of the marker coding sequence (e.g., slot blot hybridization) are also within the scope of the present invention. Reagents that bind to selected nucleic acid biomarkers can be prepared according to methods known to those of skill in the art or purchased commercially.

Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nat. Biotechnol.,* 16:381-384 (1998)), and sequencing by hybridization. Chee et al., *Science,* 274:610-614 (1996); Drmanac et al., *Science,* 260: 1649-1652 (1993); Drmanac et al., *Nat. Biotechnol.,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis.

In another embodiment, antibody reagents can be used in assays to detect expression levels of protein biomarkers of the invention in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis,* 18:2184-93 (1997); Bao, *J. Chromatogr. B. Biomed. Sci.,* 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

The expression levels of prognostic and/or predictive genes may be measure in tumor tissue. For example, the tumor tissue is obtained upon surgical removal or resection of the tumor, or by tumor biopsy. The expression level of prognostic and/or predictive genes may also be measure in tumor cells recovered from site distant from the tumor, for example circulating tumor cells or body fluid.

A detectable moiety can be used in the assays described herein (direct or indirect detection). A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by cancer biomarkers, such as antibodies, may be labeled using an appropriate marker, such as a fluorescent marker.

The 11-gene panel described herein (BAG1, BRCA1, CDC6, CDK2AP1, ERBB3, FUT3, IL11, LCK, RND3, SH3BGR, and WNT3A) provides a more accurate prognostic assay for lung cancer than other gene combinations currently known in the art. The success of different gene combinations in assigning individuals to high or low risk categories can be compared using area under the receiver operating characteristic (AUROC) analysis. AUROC is a common summary statistic that captures the ability of different models to accurately discriminate between risk groups (in this case, risk of death within 5 years of surgical resection of a lung cancer tumor).

AUROC analysis can be performed using various software programs known in the art, including, but not limited to, the R statistical computing software package and the STATA computing software package. One of skill in the art would recognize that different computing software packages may yield different c-statistics. A higher AUROC c-statistic indicates a more accurate prognostic gene signature.

Gene expression values contribute either positively to a patient's risk of mortality (represented by a hazard ratio greater than 1.0), or negatively to a patient's risk of mortality (represented by a hazard ratio less than 1.0). Thus, each gene can either increase the patient's risk of mortality, or decrease the patient's risk of mortality. Risk genes are genes for which increasing expression is associated with a higher risk of death, whereas protective genes are genes for which increasing expression is associated with a lower risk of death. In some embodiments, BAG1, BRCA1, CDC6, CDK2AP1, FUT3, IL11, and RND3 in the eleven-gene panel are risk genes that indicate an increased likelihood in mortality of the subject, whereas ERBB3, LCK, SH3BGR, and WNT3A are protective genes that indicate a decreased likelihood in mortality of the subject.

In determining the AUROC c-statistic, risk genes are assigned a positive value in the assay algorithm, such that their expression values lead to an increase in risk score, which corresponds to a greater risk of death within 5 years. Protective genes are assigned a negative value in the assay algorithm, such that their expression values lead to a decrease in risk score, which corresponds to a lower risk of death within 5 years. Further, each of the gene expression values can be weighted to represent the gene's relative contribution to a patient's risk of mortality. It should be understood that large coefficients represent genes that are very important in determining a patient's outcome, whereas smaller coefficients represent genes that contribute less to the determination of a patient's outcome. The weighted values of the combination of risk and protection genes in the eleven-gene panel described herein can be used to calculate the AUROC c-statistic.

Reports

In another aspect, the invention features a report indicating a prognosis of a subject with cancer. The report can, for example, be in electronic or paper form. The report can include basic patient information, including a subject identifier (e.g., the subject's name, a social security number, a medical insurance number, or a randomly generated number), physical characteristics of the subject (e.g., age, weight, or sex), the requesting physician's name, the date the prognosis was generated, and the date of sample collection. The reported prognosis can relate to likelihood of survival for a certain period of time, likelihood of response to certain treatments within a certain period of time (e.g., chemotherapeutic or surgical treatments), and/or likelihood of recurrence of cancer. The reported prognosis can be in the form of a percentage chance of survival for a certain period of time, percentage chance of favorable response to treatment (favorable response can be defined, e.g., tumor shrinkage or slowing of tumor growth), or recurrence over a defined period of time (e.g., 20% chance of survival over a five year period). The reported prognosis can alternatively be in the form of a calculated score. A greater or lower score, for example, can be indicative of a favorable prognosis. In another embodiment, the reported prognosis can be a general description of the likelihood of survival, response to treatment, or recurrence over a period of time (e.g., very likely, likely, or unlikely to survive for five years). In another embodiment, the reported prognosis can be in the form of a graph. In addition to the gene expression levels, the reported prognosis may also take into account additional characteristics of the subject (e.g., age, stage of cancer, gender, previous treatment, fitness, cardiovascular health, and mental health).

In addition to a prognosis, the report can optionally include raw data concerning the expression level of BAG1, BRCA1, CDC6, CDK2AP1, ERBB3, FUT3, IL11, LCK, RND3, SH3BGR, and WNT3A.

Compositions, Kits, and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Treatment Plans

Following a prognosis that provides a low-, intermediate-, or high-risk assessment of 5-year mortality, a method for determining a treatment plan can be devised. For example, once the risk assessment class has been determined, a treatment plan can be developed specific to the risk group. For example, for an individual having an expression profile of the 11 genes described herein indicative of a high-risk assessment of 5-year mortality, a health care provider can utilize a more aggressive treatment. For an individual having an expression profile of the 11 genes described herein indicative of a low-risk assessment of mortality, a health care provider can utilize a less aggressive treatment. For an individual having an expression profile of the 11 genes described herein indicative of an intermediate-risk assessment of mortality, a health care provider can utilize a treatment that is not as aggressive a high-risk assessment, but more aggressive than a low-risk assessment of 5-year mortality.

Computer Implemented System

Figure 8:
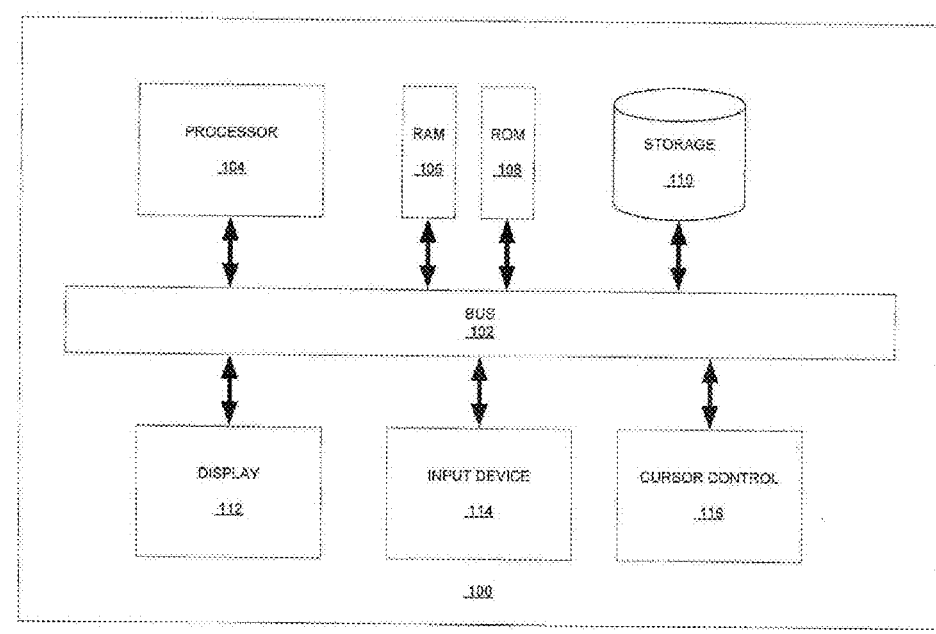
FIG. 8 is a block diagram that illustrates an exemplary computer system, in accordance with various embodiments.
Figure 9:
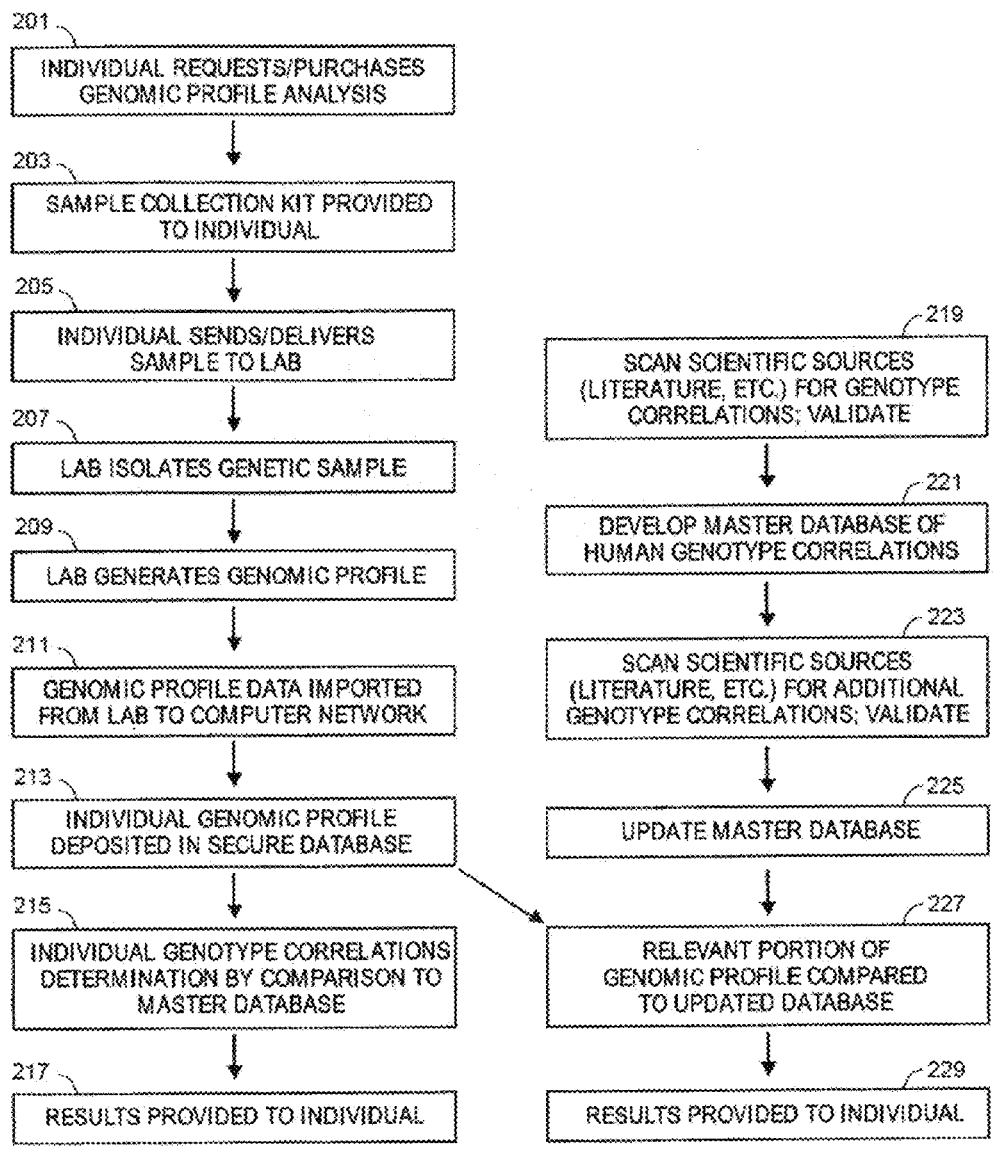
FIG. 9 is a flow chart illustrating aspects of a method according to one embodiment of the disclosure.

FIG. 8 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

EXAMPLES

The following examples are offered to illustrate, but not to limit the claimed invention.

Example 1

Prognostic Assay to Determine Risk Score in Patients with Non-Small Cell Lung Cancer (NSCLC)

A prognostic assay based on the expression patterns of 426 patients who underwent resection of stage I-IV non-small cell lung cancer (NSCLC) at the University of California, San Francisco was developed to generate a clinically useful risk score. An assay was sought that would tend to assign a higher risk score on average to patients who had succumbed to their cancer than to those who had survived the follow-up period. Patients whose sample received higher risk scores would be considered at higher risk of dying within a 5-year period after operation, whereas patients whose samples received a low score would be more likely to have survived during this time interval after their operations.

RNA was extracted from FFPE tissues samples and expression levels for target genes related to patient prognosis were assessed. A prognostic assay was then developed by correlating expression patterns of the 11 target genes related to patient prognosis (BAG1, BRCA1, CDC6, CDK2AP1, ERBB3, FUT3, IL11, LCK, RND3, SH3BGR, WNT3A) to 5-year overall survival outcomes using Cox proportional hazards modeling. 337 of the patients had non-squamous cell NSCLC. A combination of multiple 10-fold cross-validation maximizing the survival concordance index as well as L2-penalized Cox proportional hazards modeling yielded coefficients for each of the 11 target genes.

Using this model, a risk score for each patient was derived by inserting the expression levels of each of the 11 prognostic genes into the risk score algorithm that was based on the coefficients. This risk score is a continuous risk score with a range between 1 and 100 in the UCSF algorithm development cohort. Increasing risk score correlates with increasing changes of mortality within 5-years from the date of tumor resection. The Hazard Ratio of the continuous risk score is shown in Table 1. The HR of the risk score as a continuous variable is 1.184 corresponding to an 18% increase in the risk of death within 5-years of surgical resection for every point increase in the risk score (95% CI 1.123 to 1.248, p<0.0005).

TABLE 1

Hazard Ratio of the continuous risk score
Cox regression -- Breslow method for ties

| No. of subjects = | 426 | Number of obs = | 426 |
|---|---|---|---|
| No. of failures = | 187 | | |
| Time at risk = | 17366.98426 | | |
| | | LR chi2(1) = | 28.10 |
| Log likelihood = | −1058.448 | Prob > chi2 = | 0.0000 |

| t | Haz. Ratio | Std. Err. | z | P > [z] | [95% Conf. Interval] | |
|---|---|---|---|---|---|---|
| score | 1.183853 | .0319197 | 6.26 | 0.000 | 1.122916 | 1.248097 |

Risk groups were also developed based on these risk scores by placing patients into different risk categories according to their risk score. For example, cut-off points by tercile were obtained placing patients into "Low Risk", "Intermediate Risk" or "High Risk" groups based on their risk scores.

Figure 3:
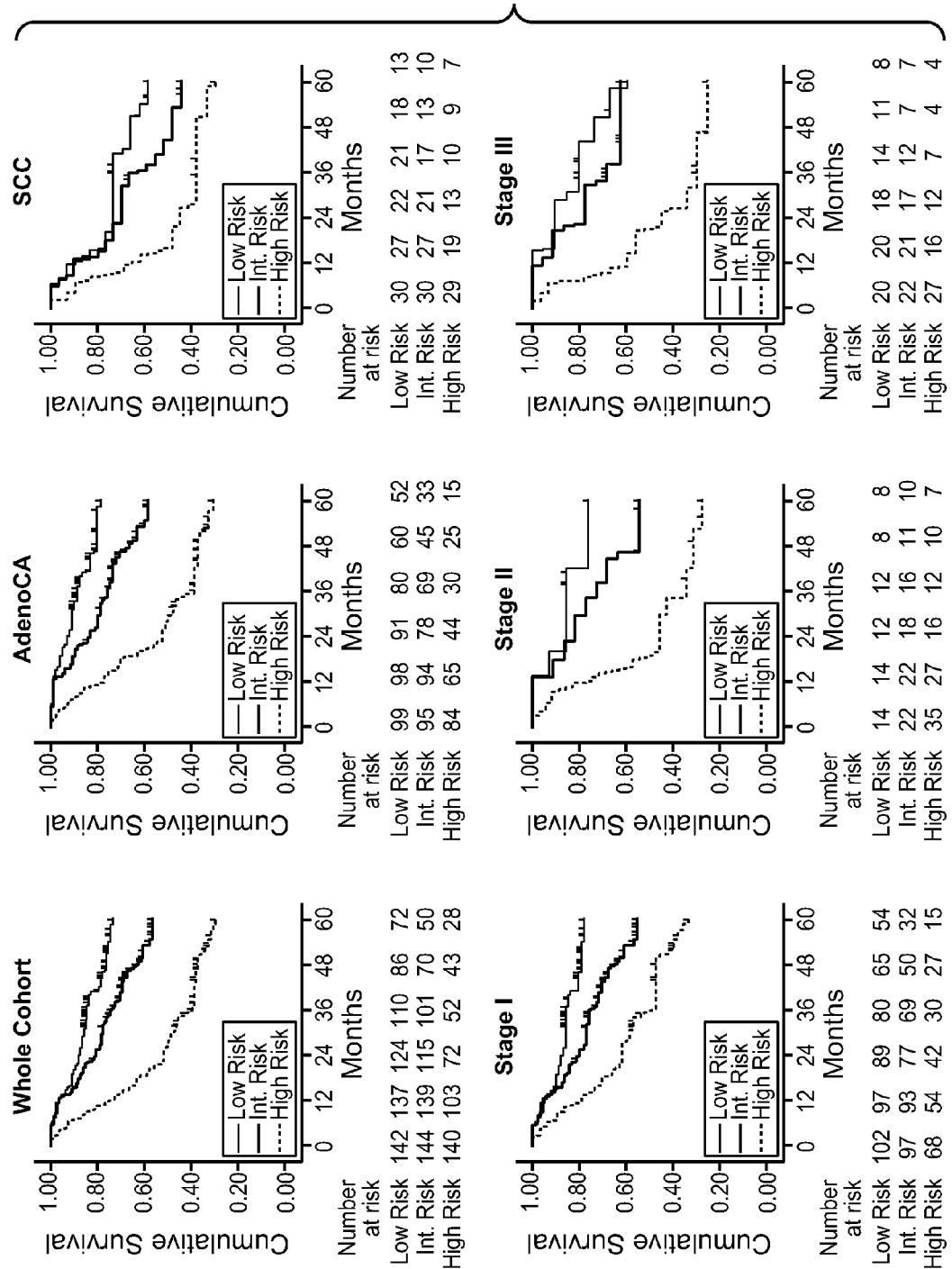
FIG. 3 is an example of a Kaplan-Meier survival analysis of Low-, Intermediate-, and High-Risk patients grouped by risk score using the algorithm in Example 1.

To assess the accuracy of these risk group assignments, Kaplan-Meier survival curves were generated for the risk groups. The Kaplan-Meier survival outcomes of these risk groups are shown in FIG. 3 and Tables 2-7.

TABLE 2

Log-rank test trend for low-, intermediate-, and
high-risk patients grouped by risk score in entire
426 UCSF algorithm development cohort.

| Time | Beg. Total | Fail | Survivor Function | Std. Error | [95% Conf. Int.] | |
|---|---|---|---|---|---|---|
| risk tercile = 0 | | | | | | |
| 0 | 0 | 0 | 1.0000 | . | . | |
| 12 | 138 | 5 | 0.9648 | 0.0155 | 0.9175 | 0.9852 |
| 24 | 125 | 13 | 0.8732 | 0.0279 | 0.8064 | 0.9182 |
| 36 | 111 | 4 | 0.8448 | 0.0304 | 0.7740 | 0.8950 |
| 48 | 87 | 10 | 0.7629 | 0.0369 | 0.6810 | 0.8264 |
| 60 | 72 | 3 | 0.7338 | 0.0391 | 0.6480 | 0.8019 |
| risk tercile = 1 | | | | | | |
| 0 | 0 | 0 | 1.0000 | . | . | |
| 12 | 140 | 5 | 0.9653 | 0.0153 | 0.9186 | 0.9854 |
| 24 | 116 | 23 | 0.8055 | 0.0330 | 0.7309 | 0.8614 |
| 36 | 101 | 9 | 0.7417 | 0.0366 | 0.6617 | 0.8056 |
| 48 | 70 | 13 | 0.6356 | 0.0417 | 0.5478 | 0.7108 |
| 60 | 50 | 7 | 0.5673 | 0.0445 | 0.4754 | 0.6490 |
| risk tercile = 2 | | | | | | |
| 0 | 0 | 0 | 1.0000 | . | . | |
| 12 | 104 | 37 | 0.7357 | 0.0373 | 0.6543 | 0.8008 |
| 24 | 73 | 31 | 0.5143 | 0.0422 | 0.4287 | 0.5933 |
| 36 | 52 | 16 | 0.3966 | 0.0416 | 0.3150 | 0.4769 |
| 48 | 44 | 3 | 0.3722 | 0.0414 | 0.2917 | 0.4526 |
| 60 | 28 | 8 | 0.2956 | 0.0409 | 0.2182 | 0.3769 |

Note:
Survivor function is calculated over full data and evaluated at indicated times; it is not calculated from aggregates shown at left.
Log-rank test for equality of survivor functions

| risk tercile | Events observed | Events expected |
|---|---|---|
| 0 | 35 | 72.61 |
| 1 | 57 | 67.92 |
| 2 | 95 | 46.47 |
| Total | 187 | 187.00 | chi2(2) = 72.61
Pr > chi2 = 0.0000
Test for trend of survivor functions chi2(1) = 64.88
Pr > chi2 = 0.0000

TABLE 3

Log-rank test trend for low-, intermediate-, and high-risk
patients grouped by risk score in the 278 patients with
adenocarcinoma in UCSF algorithm development cohort.

| Time | Beg. Total | Fail | Survivor Function | Std. Error | [95% Conf. Int.] | |
|---|---|---|---|---|---|---|
| risk tercile = 0 | | | | | | |
| 0 | 0 | 0 | 1.0000 | . | . | . |
| 12 | 99 | 1 | 0.9899 | 0.0100 | 0.9305 | 0.9986 |
| 24 | 92 | 7 | 0.9192 | 0.0274 | 0.8449 | 0.9587 |
| 36 | 81 | 3 | 0.8884 | 0.0317 | 0.8075 | 0.9366 |
| 48 | 61 | 7 | 0.8042 | 0.0418 | 0.7063 | 0.8724 |
| 60 | 52 | 1 | 0.7890 | 0.0437 | 0.6877 | 0.8608 |
| risk tercile = 1 | | | | | | |
| 0 | 0 | 0 | 1.0000 | . | . | |
| 12 | 95 | 1 | 0.9895 | 0.0105 | 0.9276 | 0.9985 |
| 24 | 79 | 15 | 0.8314 | 0.0384 | 0.7397 | 0.8931 |
| 36 | 70 | 7 | 0.7562 | 0.0442 | 0.6563 | 0.8308 |
| 48 | 46 | 7 | 0.6649 | 0.0508 | 0.5549 | 0.7537 |
| 60 | 33 | 5 | 0.5841 | 0.0561 | 0.4662 | 0.6846 |
| risk tercile = 2 | | | | | | |
| 0 | 0 | 0 | 1.0000 | . | . | |
| 12 | 66 | 19 | 0.7738 | 0.0456 | 0.6686 | 0.8493 |
| 24 | 45 | 21 | 0.5238 | 0.0545 | 0.4122 | 0.6239 |
| 36 | 30 | 11 | 0.3867 | 0.0538 | 0.2820 | 0.4900 |

TABLE 3-continued

| Time | Beg. Total | Fail | Survivor Function | Std. Error | [95% Conf. Int.] | |
|---|---|---|---|---|---|---|
| 48 | 26 | 1 | 0.3728 | 0.0536 | 0.2691 | 0.4764 |
| 60 | 15 | 4 | 0.3052 | 0.0537 | 0.2045 | 0.4117 |

Note:
Survivor function is calculated over full data and evaluated at indicated times; it is not calculated from aggregates shown at left.
Log-rank test for equality of survivor functions

| risk tercile | Events observed | Events expected |
|---|---|---|
| 0 | 19 | 45.88 |
| 1 | 35 | 39.78 |
| 2 | 56 | 24.34 |
| Total | 110 | 110.00 | chi2(2) = 58.13
Pr > ch 2 = 0.0000
Test for trend of survivor functions chi2(1) = 52.45
Pr > chi2 = 0.0000

TABLE 4

Log-rank test trend for low-, intermediate-, and high-risk patients grouped by risk score in the 89 patients with squamous cell carcinoma in UCSF algorithm development cohort

| Time | Beg. Total | Fail | Survivor Function | Std. Error | [95% Conf. Int.] | |
|---|---|---|---|---|---|---|
| risk tercile = 0 | | | | | | |
| 0 | 0 | 0 | 1.0000 | . | . | . |
| 12 | 28 | 3 | 0.9000 | 0.0548 | 0.7212 | 0.9666 |
| 24 | 23 | 5 | 0.7333 | 0.0807 | 0.5369 | 0.8567 |
| 36 | 22 | 0 | 0.7333 | 0.0807 | 0.5369 | 0.8567 |
| 48 | 19 | 2 | 0.6600 | 0.0877 | 0.4593 | 0.8010 |
| 60 | 13 | 2 | 0.5844 | 0.0926 | 0.3838 | 0.7398 |
| risk tercile = 1 | | | | | | |
| 0 | 0 | 0 | 1.0000 | . | . | . |
| 12 | 28 | 3 | 0.9000 | 0.0548 | 0.7212 | 0.9666 |
| 24 | 22 | 6 | 0.7000 | 0.0837 | 0.5026 | 0.8312 |
| 36 | 18 | 2 | 0.6296 | 0.0889 | 0.4311 | 0.7754 |
| 48 | 14 | 4 | 0.4815 | 0.0939 | 0.2914 | 0.6484 |
| 60 | 10 | 1 | 0.4444 | 0.0937 | 0.2593 | 0.6144 |
| risk tercile = 2 | | | | | | |
| 0 | 0 | 0 | 1.0000 | . | . | . |
| 12 | 20 | 10 | 0.6552 | 0.0883 | 0.4541 | 0.7973 |
| 24 | 14 | 6 | 0.4483 | 0.0923 | 0.2652 | 0.6157 |
| 36 | 11 | 2 | 0.3793 | 0.0901 | 0.2087 | 0.5490 |
| 48 | 10 | 0 | 0.3793 | 0.0901 | 0.2087 | 0.5490 |
| 60 | 7 | 2 | 0.2950 | 0.0876 | 0.1400 | 0.4687 |

Note:
Survivor function is calculated over full data and evaluated at indicated times; it is not calculated from aggregates shown at left.
Log-rank test for equality of survivor functions

| risk tercile | Events observed | Events expected |
|---|---|---|
| 0 | 12 | 18.64 |
| 1 | 16 | 17.14 |
| 2 | 20 | 12.22 |
| Total | 48 | 48.00 | chi2(2) = 7.46
Pr > chi2 = 0.0240
Test for trend of survivor functions chi2(1) = 6.99
Pr > chi2 = 0.0082

TABLE 5

Log-rank test trend for low-, intermediate-, and high-risk patients grouped by risk score in the 267 patients with stage I NSCLC in UCSF algorithm development cohort.

| Time | Beg. Total | Fail | Survivor Function | Std. Error | [95% Conf. Int.] | |
|---|---|---|---|---|---|---|
| risk tercile = 0 | | | | | | |
| 0 | 0 | 0 | 1.0000 | . | . | . |
| 12 | 98 | 5 | 0.9510 | 0.0214 | 0.8862 | 0.9793 |
| 24 | 90 | 8 | 0.8725 | 0.0330 | 0.7907 | 0.9239 |
| 36 | 81 | 1 | 0.8627 | 0.0341 | 0.7793 | 0.9163 |
| 48 | 66 | 6 | 0.7959 | 0.0409 | 0.7011 | 0.8635 |
| 60 | 54 | 1 | 0.7821 | 0.0425 | 0.6846 | 0.8527 |
| risk tercile = 1 | | | | | | |
| 0 | 0 | 0 | 1.0000 | . | . | . |
| 12 | 94 | 4 | 0.9588 | 0.0202 | 0.8939 | 0.9843 |
| 24 | 78 | 15 | 0.8040 | 0.0403 | 0.7101 | 0.8702 |
| 36 | 70 | 5 | 0.7512 | 0.0441 | 0.6521 | 0.8258 |
| 48 | 50 | 8 | 0.6565 | 0.0497 | 0.5495 | 0.7440 |
| 60 | 32 | 7 | 0.5559 | 0.0548 | 0.4421 | 0.6554 |
| risk tercile-2 | | | | | | |
| 0 | 0 | 0 | 1.0000 | . | . | . |
| 12 | 55 | 14 | 0.7941 | 0.0490 | 0.6773 | 0.8725 |
| 24 | 43 | 12 | 0.6176 | 0.0589 | 0.4915 | 0.7212 |
| 36 | 31 | 8 | 0.4924 | 0.0615 | 0.3676 | 0.6057 |
| 48 | 28 | 1 | 0.4760 | 0.0616 | 0.3518 | 0.5901 |
| 60 | 15 | 7 | 0.3367 | 0.0625 | 0.2185 | 0.4588 |

Note:
Survivor function is calculated over full data and evaluated at indicated times; it is not calculated from aggregates shown at left.
Log-rank test for equality of survivor functions

| Risk tercile | Events observed | Events expected |
|---|---|---|
| 0 | 21 | 43.59 |
| 1 | 39 | 37.53 |
| 2 | 42 | 20.88 |
| Total | 102 | 102.00 | chi2(2) = 33.33
Pr > chi2 = 0.0000
Test for trend of survivor functions chi2(1) = 32.36
Pr > chi2 = 0.0000

TABLE 6

Log-rank test trend for low-, intermediate-, and high-risk patients grouped by risk score in the 71 patients with stage II NSCLC in UCSF algorithm development cohort.

| Time | Beg. Total | Fail | Survivor Function | Std. Error | [95% Conf. Int.] | |
|---|---|---|---|---|---|---|
| risk tercile = 0 | | | | | | |
| 0 | 0 | 0 | 1.0000 | | | |
| 12 | 0 | 0 | 1.0000 | | | |
| 24 | 13 | 2 | 0.8571 | 0.0935 | 0.5394 | 0.9622 |
| 36 | 13 | 0 | 0.8571 | 0.0935 | 0.5394 | 0.9622 |
| 48 | 9 | 1 | 0.7619 | 0.1224 | 0.4209 | 0.9181 |
| 60 | 8 | 0 | 0.7619 | 0.1224 | 0.4209 | 0.9181 |
| risk tercile = 1 | | | | | | |
| 0 | 0 | 0 | 1.0000 | . | . | . |
| 12 | 0 | 0 | 1.0000 | . | . | . |
| 24 | 19 | 4 | 0.8182 | 0.0822 | 0.5853 | 0.9276 |
| 36 | 17 | 2 | 0.7273 | 0.0950 | 0.4910 | 0.8671 |
| 48 | 12 | 4 | 0.5455 | 0.1062 | 0.3207 | 0.7239 |
| 60 | 10 | 0 | 0.5455 | 0.1062 | 0.3207 | 0.7239 |

TABLE 6-continued risk tercile = 2

| | | | | | | |
|---|---|---|---|---|---|---|
| 0 | 0 | 0 | 1.0000 | . | . | . |
| 12 | 28 | 8 | 0.7714 | 0.0710 | 0.5946 | 0.8785 |
| 24 | 17 | 11 | 0.4571 | 0.0842 | 0.2890 | 0.6105 |
| 36 | 13 | 4 | 0.3429 | 0.0802 | 0.1934 | 0.4979 |
| 48 | 11 | 1 | 0.3117 | 0.0788 | 0.1682 | 0.4666 |
| 60 | 7 | 1 | 0.2771 | 0.0772 | 0.1402 | 0.4324 |

Note:
Survivor function is calculated over full data and evaluated at indicated times; it is not calculated from aggregates shown at left.
Log-rank test for equality of survivor functions

| Risk tercile | Events observed | Events expected |
|---|---|---|
| 0 | 3 | 9.24 |
| 1 | 10 | 14.10 |
| 2 | 25 | 14.66 |
| Total | 38 | 38.00 | chi2(2) = 12.89
Pr > chi2 = 0.0016

Test for trend of survivor functions chi2(1) = 12.04
Pr > chi2 = 0.0005

TABLE 7

Log-rank test trend for low-, intermediate-, and high-risk patients grouped by risk score in the 69 patients with stage III NSCLC in UCSF algorithm development cohort.

| Time | Beg. Total | Fail | Survivor Function | Std. Error | [95% Conf. Int.] | |
|---|---|---|---|---|---|---| risk tercile = 0

| 0 | 0 | 0 | 1.0000 | . | . | . |
| 12 | 0 | 0 | 1.0000 | . | . | . |
| 24 | 19 | 2 | 0.9000 | 0.0671 | 0.6560 | 0.9740 |
| 36 | 15 | 2 | 0.8000 | 0.0894 | 0.5511 | 0.9198 |
| 48 | 12 | 1 | 0.7333 | 0.1039 | 0.4680 | 0.8810 |
| 60 | 8 | 2 | 0.5926 | 0.1230 | 0.3204 | 0.7862 | risk tercile = 1

| 0 | 0 | 0 | 1.0000 | . | . | . |
| 12 | 22 | 1 | 0.9545 | 0.0444 | 0.7187 | 0.9935 |
| 24 | 18 | 4 | 0.7727 | 0.0893 | 0.5374 | 0.8985 |
| 36 | 13 | 2 | 0.6818 | 0.0993 | 0.4462 | 0.8338 |
| 48 | 8 | 1 | 0.6198 | 0.1079 | 0.3768 | 0.7911 |
| 60 | 7 | 0 | 0.6198 | 0.1079 | 0.3768 | 0.7911 | risk tercile = 2

| 0 | 0 | 0 | 1.0000 | . | . | . |
| 12 | 17 | 11 | 0.5926 | 0.0946 | 0.3863 | 0.7499 |
| 24 | 13 | 4 | 0.4444 | 0.0956 | 0.2556 | 0.6175 |
| 36 | 8 | 4 | 0.2963 | 0.0879 | 0.1406 | 0.4703 |
| 48 | 5 | 1 | 0.2469 | 0.0860 | 0.1024 | 0.4238 |
| 60 | 4 | 0 | 0.2469 | 0.0860 | 0.1024 | 0.4238 |

Note:
Survivor function is calculated over full data and evaluated at indicated times; it is not calculated from aggregates shown at left.
Log-rank test for equality of survivor functions

| risk tercile | Events observed | Events expected |
|---|---|---|
| 0 | 7 | 12.78 |
| 1 | 8 | 12.66 |
| 2 | 20 | 9.56 |
| Total | 35 | 35.00 | chi2(2) = 16.03
Pr > chi2 = 0.0003

TABLE 7-continued

Test for trend of survivor functions chi2(1) = 12.16
Pr > chi2 = 0.0005

Example 2

11-Gene Assay to Predict Survival in Resected Non-Squamous, Non-Small-Cell Lung Cancer A 14-gene assay that uses quantitative PCR analysis of formalin-fixed, paraffin-embedded (FFPE) tissues was developed with a cohort of 361 patients with non-squamous NSCLC resected at the University of California, San Francisco (UCSF). This assay included eleven biomarkers (BAG1, BRCA1, CDC6, CDK2AP1, ERBB3, FUT3, IL11, LCK, RND3, SH3BGR, and WNT3A) and three housekeeping genes (ESD, TBP, YAP1).

This assay, developed and run at an independent laboratory certified by Clinical Laboratory Improvement Amendments (CLIA), was then validated by the Kaiser Permanente Division of Research (KPDOR) with a blinded study design in a cohort of 433 patients with stage I non-squamous NSCLC resected at hospitals in the Kaiser Permanente Northern California system (CA, USA). Assay results were compared with actual patient outcomes independently by the KPDOR. International, independent large-scale validation of this molecular prognostic assay was also done in a cohort of 1006 Chinese patients who had undergone resection of early-stage NSCLC at one of several institutions participating in the China Clinical Trials Consortium (CCTC).

Patients were eligible to enter the study as part of the training cohort if they underwent surgical resection of non-squamous NSCLC at UCSF with curative intent between Jan. 1, 1997, and Dec. 31, 2007.

Patients were eligible to be included in the Kaiser Permanente validation cohort if they underwent complete resection of American Joint Commission on Cancer stage I non-squamous NSCLC by clinical and pathological staging at a Northern California Kaiser Permanente facility between Jan. 1, 1998, and Dec. 31, 2005.

Patients were eligible to be included in the CCTC validation cohort if they had undergone an attempt at curative resection for American Joint Commission on Cancer stage I-III non-squamous-cell NSCLC at either First Affiliated Hospital of Guangzhou Medical College (Guangdong, China), Sun Yat-sen University Cancer Centre in Guangzhou (Guangdong, China), or Shanghai Pulmonary Hospital (Shanghai, China) between Jan. 1, 2000, and Dec. 31, 2008.

Exclusion criteria for patients in either the training or validation cohorts were as follows: missing or inadequate tissue blocks (i.e., a tumor that occupies <25% of the tissue surface area), death within 30 days of resection, treatment with preoperative chemotherapy (validation cohorts only), positive margins on pathology (validation cohorts only), and a second cancer (excluding cutaneous basal and squamous-cell carcinomas) diagnosed within 3 years of the lung cancer diagnosis (CCTC validation cohort only). Information on clinical variables, follow-up, and cause of death were obtained from a review of medical records. Vital status and date of death were established by review of medical records and verified by sources including the Kaiser Permanente Northern California Cancer Registry, California Death Records, Social Security Death Master File, and direct contact with the patient or their family.

Sample Preparation and Analysis

Six 10-micron FFPE sections were used per sample. Samples were stripped of paraffin by the use of xylene, then incubated with proteinase K (MasterPure RNA Purification Kit, Epicentre, Madison, Wis.) at 65° C. for 2 hours. Protein precipitation and alcohol-based nucleic acid precipitation was performed using the MasterPure RNA Purification Kit (Epicentre, Madison, Wis.). RNA extracts were DNase-treated and purified using silica-gel membrane spin columns (RNEeasy Micro Kit, Qiagen, Valencia, Calif.).

To control for RNA degradation that can occur in FFPE samples, RNA quantity and quality was measured using a Nanodrop spectrophotometer (Thermo Scientific, Wilmington, Del.). Extracted RNA underwent reverse transcription (iScript Select cDNA Synthesis Kit, BioRad Laboratories, Hercules, Calif.) using gene-specific primers. Gene-specific primers were 9-13 mer truncated versions of the reverse qPCR primers optimized for an annealing temperature of 42° C. cDNA underwent 10 cycles of preamplification (TaqMan PreAmp Master Mix, Applied Biosystems, Carlsbad, Calif.) prior to qPCR.

TaqMan quantitative PCR assays (BioSearch Technologies, Novato, Calif.) custom-designed for use on RNA extracted from FFPE tissues were used to quantify RNA expression using FAST chemistry on a 7900HT Fast Real-Time PCR System (Applied Biosystems, Carlsbad, Calif.). FFPE-specific TaqMan quantitative PCR assays were designed to target 65-85 base pair amplicons that crossed exon-exon boundaries, avoiding template structures and cross-homologies (Beacon Designer 5.0, Premier Biosoft, Palo Alto, Calif.). All primer sequences underwent a BLAST search against the human genome (NCBI ref_assembly 37.1) to ensure target specificity. Synthesized primers were tested for optimal primer concentrations and single product dissociation using SYBR green melting curves.

All RNA expression measurements were normalized to commercially-available RNA extracted from pooled frozen normal lung samples (Clontech, Laboratories, Mountain View, Calif.) and the relative expression for each target gene was calculated using the comparative $C_T$ method. The average $C_T$ value of the three housekeeping genes ESD, TBP, and YAP1 was used to normalize gene expression and calculate delta $C_T$ values.

Development of the Prognostic Algorithm

Eleven cancer-related target genes (BAG1, BRCA1, CDC6, CDK2AP1, ERBB3, FUT3, IL11, LCK, RND3, SH3BGR, and WNT3A) and three reference genes (ESD, TBP, and YAP1) were evaluated in the UCSF training cohort. See FIG. 4.

L2-penalized Cox proportional hazards modeling (R package glmnet v1.5.3) was the primary analytical tool used to develop the coefficients in the prognostic algorithm using the relative expression values of the eleven target genes in the UCSF FFPE cohort. The amount of L2-penalty applied was determined using 10-fold cross-validation. A continuous risk score was generated for each subject based on model coefficients. A conventional linear risk model was used in which each relative gene expression level (delta-delta $C_T$) was multiplied by its coefficient; these products were then summed resulting in a single raw risk score.

Raw Risk Score=delta-delta $C_{T\ BAG1}$*model coefficient$_{BAG1}$+delta-delta $C_{T\ BRCA1}$*model coefficient$_{BRCA1}$+delta-delta $C_{T\ CDC6}$*model coefficient$_{CDC6}$+delta-delta $C_{T\ CDK2AP1}$*model coefficient$_{CDK2AP1}$+delta-delta $C_{T\ ERBB3}$*model coefficient$_{ERBB3}$+delta-delta $C_{T\ FUT3}$*model coefficient$_{FUT3}$+delta-delta $C_{T\ IL11}$*model coefficient$_{IL11}$+delta-delta $C_{T\ LCK}$*model coefficient$_{LCK}$+delta-delta $C_{T\ RND3}$*model coefficient$_{RND3}$+delta-delta $C_{T\ SH3BGR}$*model coefficient$_{SH3BGR}$+delta-delta $C_{T\ WNT3A}$*model coefficient$_{WNT3A}$ The raw risk score was then scaled using a linear function based on the minimum and maximum raw risk scores, producing a single integrated Risk Score that fell on a scale of 1-100.

Risk Score=39.39747*Raw Risk Score−16.94965+1

Resultant predicted risk scores were divided at the 33$^{rd}$ and 67$^{th}$ percentiles to generate low-, intermediate-, and high-risk groups. A complete table of the algorithm coefficients, scaling coefficients, and risk category cut-off values is given in Table 8 below.

TABLE 8

Summary of algorithm coefficients, scaling coefficients, and risk category cut-off values derived from UCSF training cohort

|  | Value |
|---|---|
| Gene Coefficients |  |
| BAG1 | −0.0023688 |
| BRCA1 | −0.1460735 |
| CDC6 | −0.0833502 |
| CDK2AP1 | −0.1865318 |
| ERBB3 | 0.0663762 |
| FUT3 | −0.0345802 |
| IL11 | −0.0138303 |
| LCK | 0.2098769 |
| RND3 | −0.0884906 |
| SH3BGR | 0.1982098 |
| WTN3A | 0.1185592 |
| Scaling coefficients |  |
| Slope | 39.39747 |
| Intercept | −16.94965 |
| Risk Category Cut-off Values |  |
| Low-Intermediate Cut-off | 23.81960 |
| Intermediate-High Cut-off | 36.87494 |

Risk scores were generated and risk categories were assigned using the same gene coefficients, scaling coefficients, and cut-off values in the validation cohorts. As the limits of the Risk Scare scale were 1 and 100 based on the range of the UCSF training cohort, any Risk Score less than 1 was assigned a Risk Score of 1 while any Risk Score greater than 100 was assigned a Risk Score of 100).

Assay Robustness and Validation

The molecular assay was developed, completely specified, and analytically validated in a CLIA-certified laboratory prior to the initiation of the blinded clinical validation study. Nanodrop concentration and purity cut-off values for the RNA were determined empirically by assessing over 400 samples whose average housekeeping raw expression values fell within a pre-specified raw $C_T$ range. Concentration, 260/280 ratio, and 260/230 ratio cut-offs were determined by eliminating the lowest 2.5% for each individual parameter ranked from lowest to highest, and then taking the next highest measurement to be the acceptable cut-off number. In addition, the average housekeeping gene raw $C_T$ was calculated for every sample. Only samples whose average housekeeping raw expression values fell within a pre-specified range were included in the study. In order to obtain this range, the expression of 442 FFPE lung cancer samples obtained from UCSF was studied. The average housekeeping gene $C_T$ value for these samples ranged between 17.79-37.76, with a mean value of 23.94 and a standard deviation of 2.66. The pre-specified range was determined by taking the mean housekeeping gene $C_T$ plus or minus three standard deviations.

Each PCR plate was run with a positive control (commercially-available RNA extracted from pooled frozen normal lung samples (Clontech, Laboratories, Mountain View, Calif.) as well as a negative (no-template) control. Each sample was run with a TaqMan assay designed to detect genomic contamination. Repeated testing of the molecular prognostic assay on FFPE samples on different days and on different sections of the same tumor demonstrated high reproducibility of the Risk Score, with an average standard deviation of 2.18 units (range between 0.83-4.62) on a 100-unit scale.

The inclusion criteria of greater than 25% tumor was empirically derived by categorizing samples into 25-50% tumor, 50-75% tumor, and >75% tumor. The hazard ratio of the high-risk group compared to the low-risk group for each of these percentage categories is shown in Table 9 below.

TABLE 9

Hazard ratio of the high-risk category by percent tumor

| Percent Tumor | Risk Category HR[§] | 95% CI | p-value |
|---|---|---|---|
| 25-50% | 2.39 | 1.65-3.47 | <0.0001 |
| 50-75% | 2.31 | 1.57-3.28 | <0.0001 |
| >75% | 2.40 | 1.52-3.79 | <0.0001 |

[§]Modeled as a continuous variable

Statistical Analysis

The overall survival from the time of resection was chosen as the primary endpoint. A secondary endpoint in the Kaiser validation cohort was lung-cancer-specific mortality. The primary predictor assessed was the risk category assigned by the molecular assay. Other important covariates, including age, sex, smoking history, histology, tumor size, and disease stage, were compared with outcome by use of univariate and multivariate Cox proportional hazards modelling. Wald and nested likelihood ratio tests were done for univariate and multivariate modelling, respectively, to assess statistical significance. Nested likelihood ratio tests are more appropriate for multivariate models because they examine whether the addition of a new variable, such as the molecular test, offers an improvement in fit beyond standard clinical variables such as age, sex, and tumor size. Stratified Kaplan-Meier analysis with a right-censored dataset and the log-rank test for trend were used to assess the association between risk category and the primary and secondary endpoints. For all statistical tests, a pre-specified two-sided a of 0.05 was regarded as statistically significant. Time-dependent area under the receiver operating characteristic curve (AUROC) was calculated with the survcomp (version 1.1.6) package in R; differences in AUROCs were tested by multivariate Cox proportional hazards modelling and compared by use of integrated AUROCs with the Wilcoxon rank sum test.

A power calculation for the UCSF training and Kaiser Permanente validation cohorts was performed using the following assumptions: β of 0.9, risk category population standard deviation of 0.8, a hazard ratio of 1.5 for the high-risk group, probability of withdrawal of 0.2, and event probabilities of 0.4 (UCSF stage I-III training cohort) and 0.3 (Kaiser stage I validation cohort). The power calculation resulted in an estimated sample size of 313 and 417 patients for the UCSF and Kaiser Permanente cohorts respectively. As the proportion of successful RNA extraction was not known prior to the start of the study, a 10% failure rate was assumed which yielded a final sample size of 344 patients for the UCSF training cohort.

Analyses were done with the programming languages R29 (version 2.12.2 for Macintosh) and Stata/MP (version 11).

Results

A total of 399 patients were identified who had undergone resection of non-squamous NSCLC at UCSF during the study period; of these, 361 met criteria for inclusion in the training cohort. 460 patients at Kaiser Northern California had undergone resections of stage non-squamous NSCLC, of whom 433 met criteria for inclusion in the independent validation cohort. 1006 patients were identified in the CCTC institutions that met criteria for inclusion in that validation study. Relevant clinical and pathological characteristics of these patients are shown in Table 10 below. The rate of successful RNA extraction was high in all three cohorts.

TABLE 10

Clinical and pathological characteristics of patients

| | UCSF training cohort | Kaiser validation cohort | CCTC validation cohort |
|---|---|---|---|
| FFPE blocks available | 361 | 433 | 1006 |
| Successful RNA recovery | 337 (93%) | 420 (97%) | 967 (96%) |
| Age at resection (years; mean [SD]) | 67.4 (11) | 66.6 (9) | 58.3 (11) |
| Sex (female) | 200 (59%) | 229 (55%) | 366 (38%) |
| Smoking history | | | |
| Yes | 224 (66%) | 355 (85%) | 492 (49%) |
| No | 57 (17%) | 36 (9%) | 403 (40%) |
| Unknown | 56 (17%) | 29 (7%) | 72 (7%) |
| Survivor follow-up (months; median [IQR]) | 64.0 (45.6-88.9) | 106.0 (88.0-125.0) | 53.4 (37.4-68.0) |
| Deaths at 5 years from resection | 139 (41%) | 179 (43%) | 406 (42%) |
| Histology | | | |
| Adenocarcinoma | 278 (83%) | 325 (77%) | 881 (88%) |
| Large cell | 17 (5%) | 15 (4%) | 17 (2%) |

TABLE 10-continued

Clinical and pathological characteristics of patients

|  | UCSF training cohort | Kaiser validation cohort | CCTC validation cohort |
|---|---|---|---|
| Mixed | 10 (3%) | 15 (4%) | 46 (5%) |
| NSCLC (not otherwise specified) | 32 (10%) | 65 (16%) | 23 (2%) |
| Stage | | | |
| I | 223 (66%) | 420 (100%) | 471 (47%) |
| Ia | 152 (45%) | 285 (68%) | 239 (24%) |
| Ib | 71 (21%) | 135 (32%) | 232 (23%) |
| II | 41 (12%) | 0 | 222 (22%) |
| IIa | 14 (4%) | 0 | 69 (7%) |
| IIb | 27 (8%) | 0 | 153 (15%) |
| III | 58 (17%) | 0 | 266 (26%) |
| IIIa | 32 (10%) | 0 | 247 (25%) |
| IIIb | 26 (8%) | 0 | 19 (2%) |
| IV | 9 (3%) | 0 | 0 |
| Undetermined | 6 (2%) | 0 | 8 (1%) |

Data are n (%), unless otherwise stated.
CCTC = China Clinical Trials Consortium.
FFPE = formalin-fixed, paraffin-embedded.
NSCLC = non-small-cell lung cancer.
UCSF = University of California, San Francisco.

During rigorous technical validation and establishment of the assay, candidate gene expression analysis and comparison with patients' outcomes was shown to be similar in groups of tissue blocks in which the tumor occupied either 25-50%, 50-75%, or more than 75% of the tissue surface area.

Figure 5A:
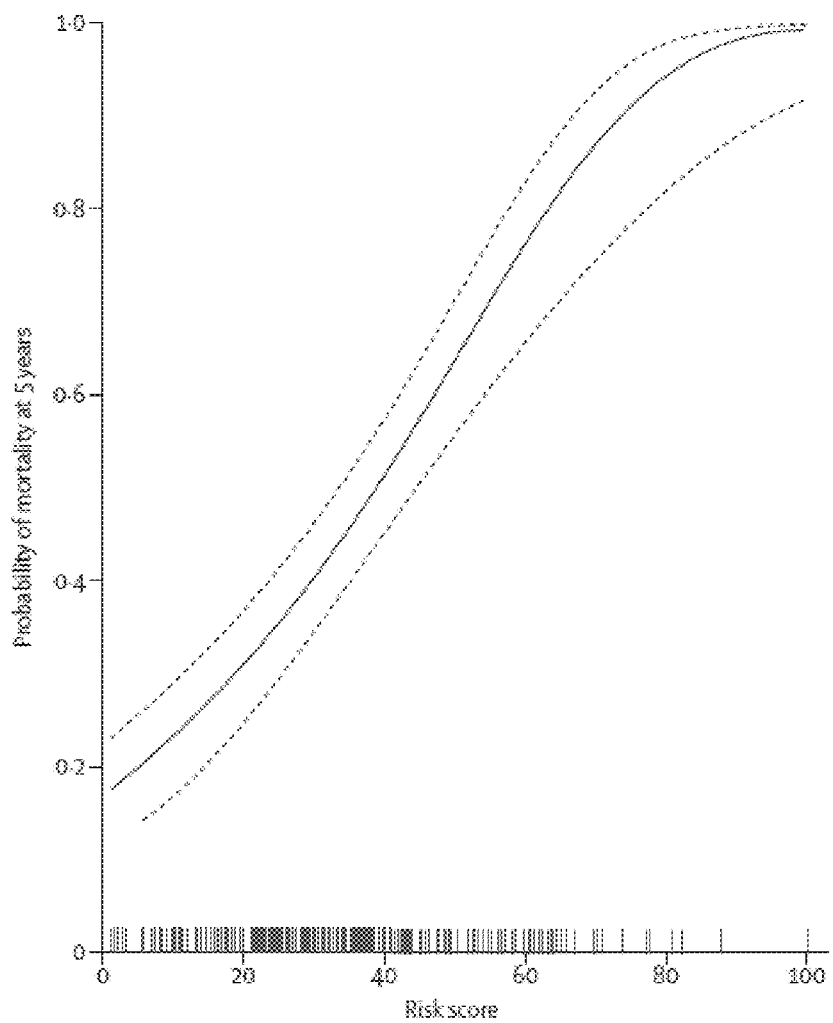
FIG. 5A is a graph illustrating the probability of mortality at 5 years by risk score, where dashed lines are 95% confidence intervals (CIs), and hash marks above the x-axis are individual risk scores for every patient.
Figure 5B:
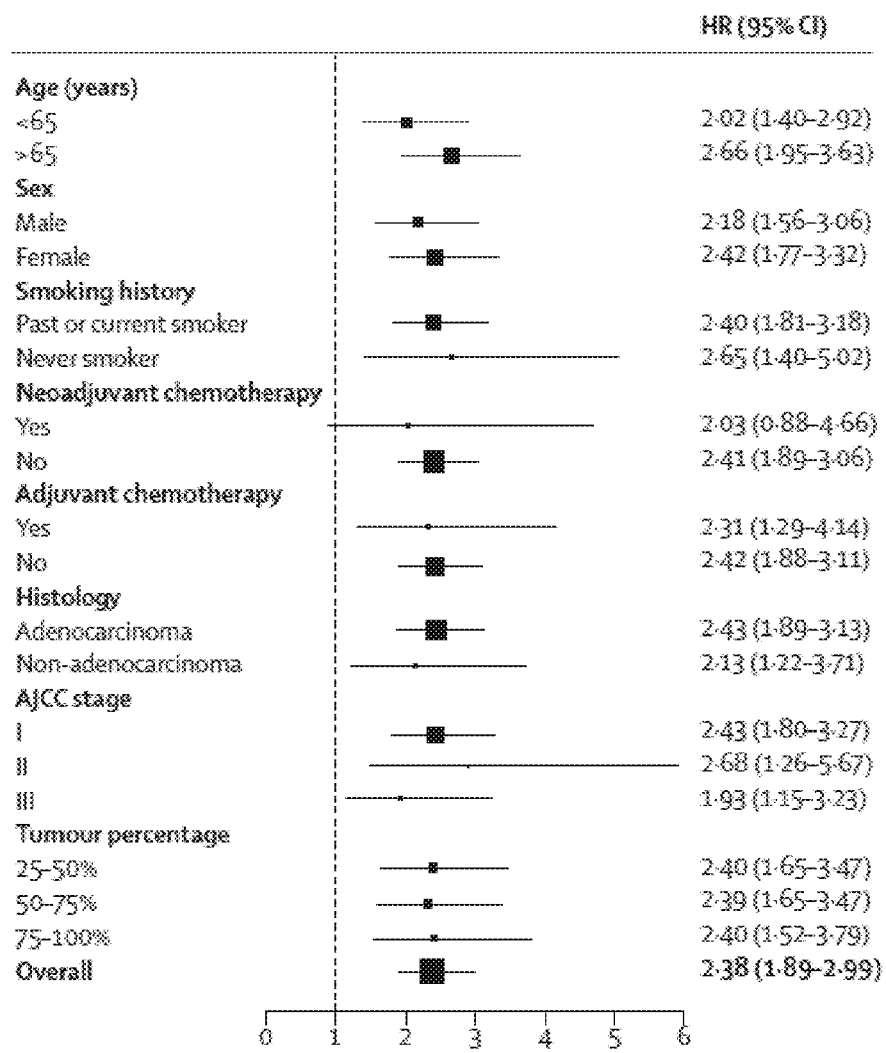
FIG. 5B is a graph illustrating the increase in 5-year overall mortality hazard ratio (HR) by subgroup for each stepwise increase in risk category (e.g., low to intermediate, and intermediate to high), where box sizes are proportional to group size and AJCC refers to American Joint Committee on Cancer.

Individual risk scores were calculated for every patient in the UCSF training cohort. Higher risk scores were positively associated with increased probability of mortality at 5 years. With reference to FIGS. 5A and 5B, it should be understood that a hazard ratio greater than 1 implies that more patients in the high-risk group are dying at any time compared with the low-risk group, whereas a hazard ratio of less than 1 means that fewer patients in the high-risk group are dying at any time compared with the low-risk group.

To better identify patients at highest and lowest risk, cutoff values defining low-risk, intermediate-risk, and high-risk groups were derived by dividing the training cohort risk scores into tertiles. With reference again to FIGS. 5A and 5B, a higher risk of morality with each increase in risk category was observed in almost every subgroup of the UCSF training cohort, and correlation of risk score to clinical outcome was much the same in samples with 25-50%, 50-75%, and >75% tumor surface area.

After the assay was fully specified, technical validation was done by the CLIA-certificated laboratory. The KPDOR and the CCTC then performed independent, blinded validations of the technically validated assay. Samples were sent by the KPDOR to the CLIA-certified laboratory for blinded testing and assignment of a risk category, and the assay's performance. By contrast with the empirical ratio (1:1:1) of low-risk, intermediate-risk, and high-risk patients in the training cohort, a greater proportion of high-risk patients was identified in the Kaiser Permanente validation cohort.

This finding might be attributable to the lower 5 year overall survival of the Kaiser stage I validation cohort (56.4%) compared with the stage I UCSF training cohort (61.9%). In the Kaiser Permanente validation cohort, Kaplan-Meier survival analysis showed 5 year survival of 71.4% (95% CI 60.5-80.0) in the low-risk group, 58.3% (48.9-66.6) in the intermediate-risk group, and 49.2% (42.2-55.8) in the high-risk group. A sensitivity analysis that excluded the 18 patients in the Kaiser Permanente validation cohort who received adjuvant chemotherapy gave 5 year survival outcomes that were much the same: 70.0% (58.7-78.8) in the low-risk group, 58.2% (48.5-66.7) in the intermediate-risk group, and 48.9% (41.7-55.6) in the high-risk group ($p_{trend}$=0.0006). 5 year lung-cancer-specific survival was 84.6% (74.4-91.0) in the low-risk group, 70.3% (60.6-78.0) in the intermediate-risk group, and 63.3% (55.8-69.8) in the high-risk group. A Kaplan-Meier survival analysis was also performed for patients with stage I disease in the Kaiser validation cohort who had no high-risk National Comprehensive Cancer Network (NCCN) criteria. This group included all patients with stage IA disease and a subgroup of patients with stage IB disease. The 5 year overall survival for the patients in this subgroup (with risk staging as per molecular assay results) was 72.7% (61.3-81.3) in the low-risk group, 59.0% (48.9-67.8) in the intermediate-risk group, and 50.4% (42.0-58.3) in the high-risk group.

Figure 6A:
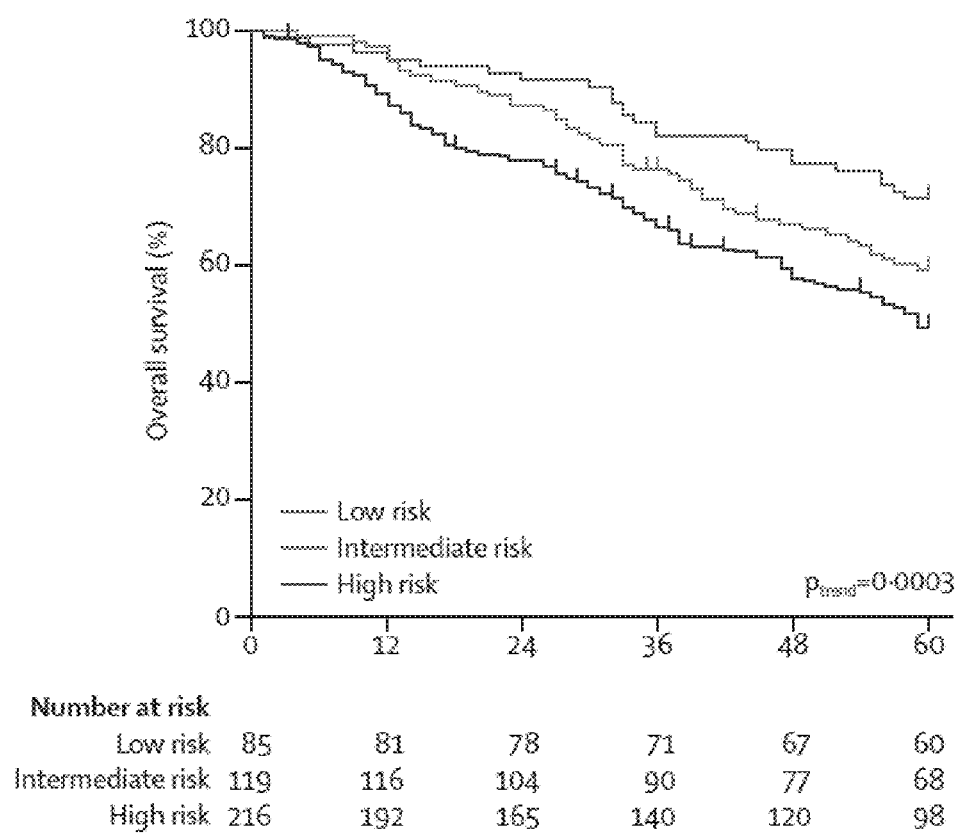
FIG. 6A is a graph illustrating the overall survival for the entire cohort.
Figure 6B:
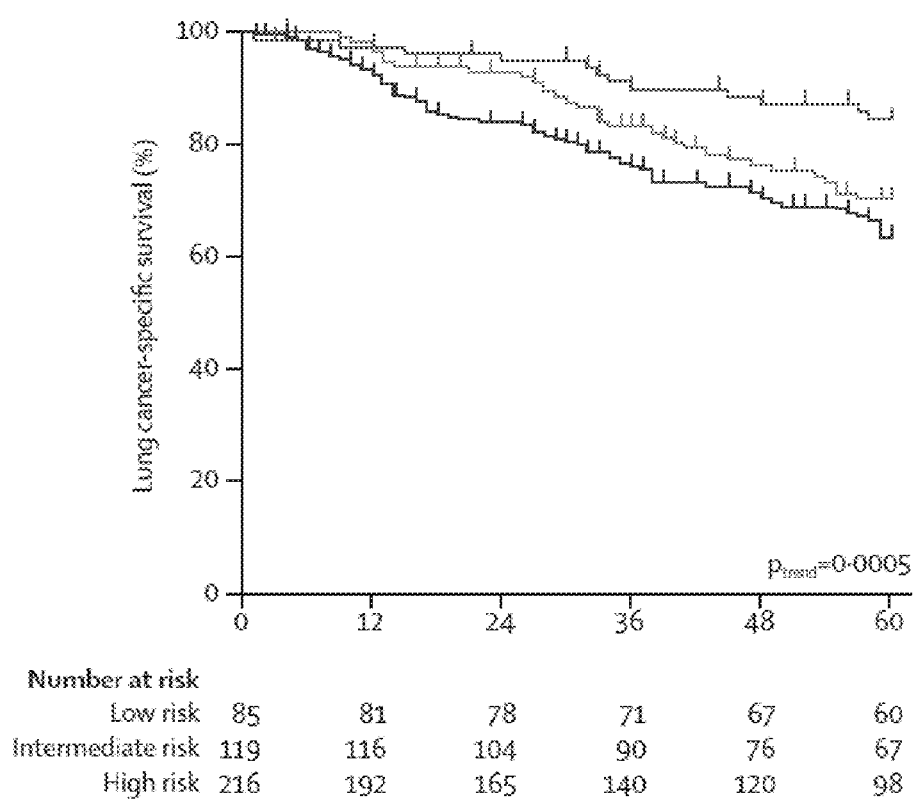
FIG. 6B is a graph illustrating the lung-cancer-specific survival for the entire cohort, in which non-lung cancer deaths were censored.
Figure 6C:
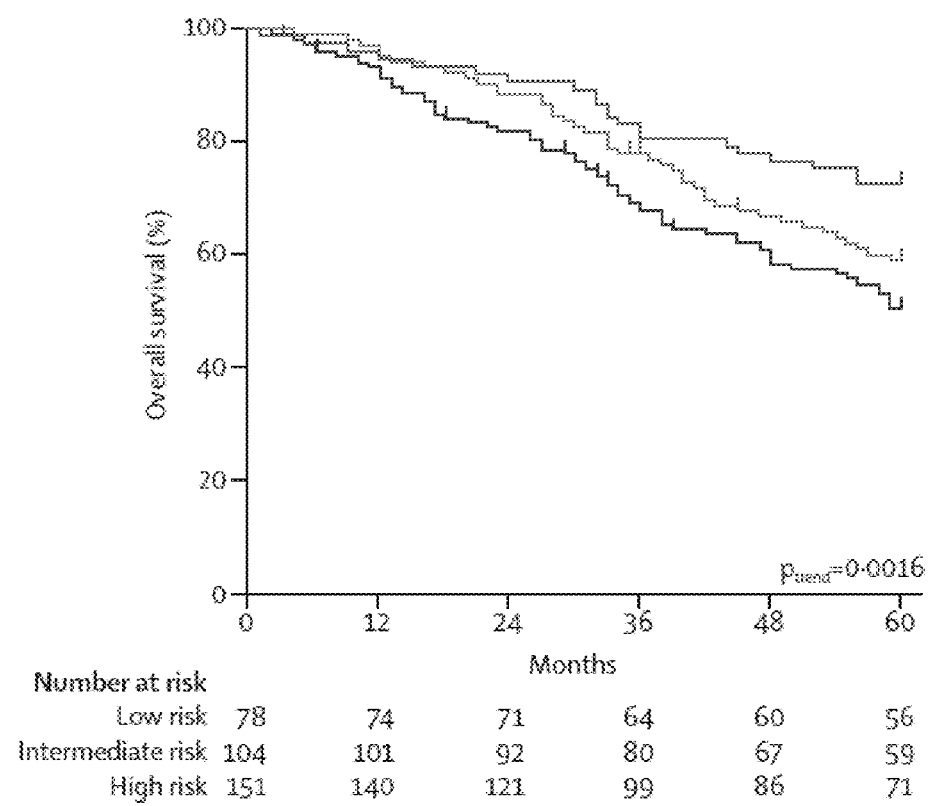
FIG. 6C is a graph illustrating the overall survival for 330 patients with American Joint Commission on Cancer stage IA and IB disease considered to be low risk as per conventional pathological criteria (National Comprehensive Cancer Network).

With reference to FIG. 6A, the median survival was observed to be 113 months in the low-risk group, 91 months in the intermediate-risk group, and 59 months in the high-risk group. With reference to FIG. 6B, median lung cancer-specific survival was not observed to be reached in any risk group. The mortality incidence rate was 2.7 per 100 person-years in the low-risk group, 5.0 per 100 person-years in the intermediate-risk group, and 6.6 per 100 person-years in the high-risk group. With reference to FIG. 6C, median survival was 113 months in the low-risk group, 88 months in the intermediate-risk group, and 70 months in the high-risk group.

In the Kaiser Permanente validation cohort, risk category (high), age, and sex were statistically significant predictors of mortality in univariate analysis, as seen in Table 11 below.

TABLE 11

Cox proportional hazard models for 5 year overall mortality
in the Kaiser Permanente validation cohort

|  | Univariate analysis | | Multivariate analysis | |
| --- | --- | --- | --- | --- |
|  | Hazard ratio (95% CI) | Wald test p value | Hazard ratio (95% CI) | Likelihood ratio test p value |
| Risk category* | | | | |
| High risk | 2.16 (1.39-3.36) | 0.0007 | 2.04 (1.28-3.26) | 0.0016 |
| Intermediate risk | 1.60 (0.98-2.60) | 0.0610 | 1.66 (1.00-2.74) | 0.0436 |
| Age >65 years | 1.55 (1.14-2.10) | 0.0054 | 1.66 (1.21-2.29) | 0.0016 |
| Sex (female) | 0.55 (0.41-0.74) | 0.0001 | 0.67 (0.49-0.92) | 0.0123 |
| Never smoker | 0.59 (0.32-1.09) | 0.0917 | 0.83 (0.44-1.55) | 0.5438 |
| Histology† | | | | |
| Large-cell carcinoma | 0.96 (0.42-2.17) | 0.9139 | 0.64 (0.26-1.59) | 0.3038 |
| Mixed | 0.98 (0.43-2.22) | 0.9615 | 0.85 (0.37-1.95) | 0.6932 |
| NSCLC (not otherwise specified) | 1.13 (0.89-1.93) | 0.1659 | 1.18 (0.79-1.75) | 0.4320 |
| Tumour size >4 cm | 1.42 (0.97-2.07) | 0.0697 | 1.10 (0.73-1.66) | 0.6435 |

NSCLC = non-small-cell lung cancer.
*Compared with low-risk group.
†Compared with adenocarcinoma.

Multivariate analysis (adjusting for age, sex, smoking history, histology, and tumor size >4 cm) showed that both high-risk and intermediate-risk groupings as well as age and sex were statistically significant predictors of mortality, as seen in Table 12 below.

TABLE 12

Multivariate cox proportional hazards model for
5-year overall mortality in the Kaiser Permanente
validation cohort excluding the molecular test

|  | HR | 95% CI | LR test p-value |
| --- | --- | --- | --- |
| Age >65 | 1.59 | 1.16-2.20 | 0.0036 |
| Female Sex | 0.65 | 0.47-0.89 | 0.0064 |
| Never Smoker | 0.74 | 0.40-1.38 | 0.3294 |
| Histology§ | | | |
| Large Cell Carcinoma | 0.76 | 0.31-1.87 | 0.5346 |
| Mixed | 1.00 | 0.44-2.27 | 0.9933 |
| NSCLC NOS | 1.26 | 0.85-1.88 | 0.2555 |
| Tumor Size >4 cm | 1.21 | 0.81-1.80 | 0.3608 |

§Compared to Adenocarcinoma

Figure 7:
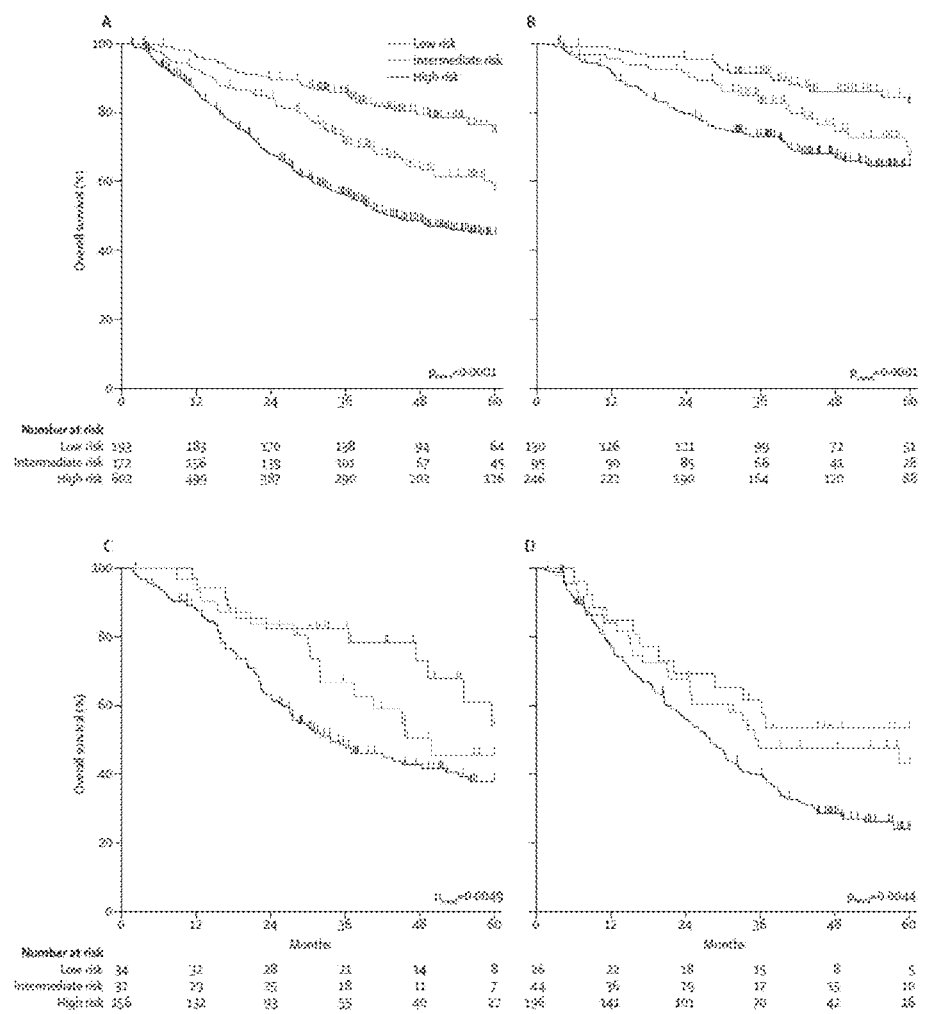
FIG. 7 shows graphs that depict (A) overall survival for the entire cohort, and survival in patients with (B) stage I, (C) stage II, and (D) stage III disease.

In the CCTC cohort, 5-year mortality after complete resection of non-squamous-cell NSCLC by risk group (defined according to results of the molecular assay) were as follows: 74.1% (66.0-80.6) in the low-risk group, 57.4% (48.3-65.5) in the intermediate-risk group, and 44.6% (40.2-48.9) in the high-risk group, as seen in FIG. 7.

Median survival was 101.1 months in the low-risk group, 77.2 in the intermediate-risk groups, and 43.1 months in the high-risk group. An improvement with the use of the 14-gene prognostic assay compared with use of traditional staging is suggested by the statistically significant separation of Kaplan-Meier survival curves for 5 year overall survival between low-risk, intermediate-risk, and high-risk patients in subgroup analyses of patients with different stage disease (see FIG. 7): stage I disease (low risk=83.0% [73.8-89.1]; intermediate risk=67.7% [54.8-77.7]; high risk=64.6% [57.9-70.5]), stage II disease (low risk=54.2% [30.1-73.2]; intermediate risk=45.8% [26.2-63.4]; high risk=38.1% [29.4-46.8]), and stage III disease (low risk=53.3% [32.6-70.3]; intermediate risk=43.3% [27.2-58.5]; high risk=24.0% [17.5-30.9]). Univariate Cox proportional hazards modelling indicated that sex (male), smoking history, large and mixed cell histology, and disease stage all had a negative effect on survival in the CCTC cohort, as seen in Table 13 below.

TABLE 13

Cox proportional hazards model for 5 year overall mortality
in the China Clinical Trials Consortium validation cohort

|  | Univariate analysis | | Multivariate analysis | |
| --- | --- | --- | --- | --- |
|  | Hazard ratio (95% CI) | Wald test p value | Hazard ratio (95% CI) | Likelihood ratio test p value |
| Risk category* | | | | |
| High risk | 3.07 (2.21-4.25) | <0.0001 | 2.37 (1.63-3.43) | <0.0001 |
| Intermediate risk | 1.87 (1.26-2.77) | 0.0019 | 1.60 (1.03-2.49) | 0.0354 |
| Age >65 years | 1.11 (0.90-1.37) | 0.3337 | 1.19 (0.94-1.49) | 0.1493 |
| Sex (female) | 0.78 (0.63-0.95) | 0.0150 | 0.93 (0.70-1.23) | 0.6057 |
| Never smoker | 0.70 (0.56-0.86) | 0.0009 | 0.84 (0.64-1.10) | 0.1986 |
| Histology† | | | | |
| Large-cell carcinoma | 2.12 (1.09-4.11) | 0.0259 | 1.68 (0.83-3.41) | 0.1831 |
| Mixed | 1.67 (1.12-2.48) | 0.0118 | 1.07 (0.69-1.64) | 0.7714 |

TABLE 13-continued

Cox proportional hazards model for 5 year overall mortality in the China Clinical Trials Consortium validation cohort

|  | Univariate analysis | | Multivariate analysis | |
| --- | --- | --- | --- | --- |
|  | Hazard ratio (95% CI) | Wald test p value | Hazard ratio (95% CI) | Likelihood ratio test p value |
| NSCLC (not otherwise specified) | 0.89 (0.44-1.80) | 0.7528 | 0.77 (0.36-1.63) | 0.4759 |
| Stage‡ | 1.44 (1.35-1.53) | <0.0001 | 1.43 (1.33-1.53) | <0.0001 |

NSCLC = non-small-cell lung cancer.
*Compared with low-risk category.
†Compared with adenocarcinoma.
‡Modelled as a continuous variable.

None of these factors, however, was observe to have as great an effect on survival as designation in the high-risk category according to the molecular assay. Multivariate analysis showed that high-risk and intermediate-risk designation remained a statistically significant predictor of survival even after adjusting for age, sex, smoking history, histology, and disease stage. See Tables 14-16 below.

TABLE 14

Tabulation of risk factors by risk category in the Kaiser Permanente validation cohort

|  | Low-Risk | Intermediate-Risk | High-Risk | P value |
| --- | --- | --- | --- | --- |
| Number of Patients | 85 | 119 | 216 |  |
| Age at Resection | 66.6 (9.8)§ | 67.1 (8.9)§ | 66.2 (9.3)§ | 0.7114* |
| Sex |  |  |  |  |
| Male | 28 (32.9) | 51 (42.9) | 112 (51.9) | 0.0098 |
| Female | 57 (67.1) | 68 (57.1) | 104 (48.1) |  |
| Smoking History |  |  |  |  |
| Yes | 68 (80.0) | 100 (84.0) | 187 (86.6) | 0.1096 |
| No | 12 (14.1) | 10 (8.4) | 14 (6.5) |  |
| Histology |  |  |  |  |
| Adenocarcinoma | 77 (90.6) | 95 (79.8) | 153 (70.8) | 0.0070 |
| Large Cell | 0 | 2 (1.7) | 13 (6.0) |  |
| Mixed | 2 (2.4) | 3 (2.5) | 10 (4.6) |  |
| NSCLC NOS | 6 (7.1) | 19 (16.0) | 40 (18.5) |  |
| Tumor Size (cm) | 2.3 (1.4)§ | 2.6 (1.6)§ | 3.4 (1.8)§ | <0.0001* |
| Stage |  |  |  |  |
| Ia | 70 (82.4) | 95 (79.8) | 120 (55.6) | <0.0001 |
| Ib | 15 (17.6) | 24 (20.2) | 96 (44.4) |  |

Numbers in paratheses represent the percentage of patients in each risk category except where stated.
§Cohort Mean (Standard Deviation)
*ANOVA test

TABLE 15

Multivariate cox proportional hazards model for 5-year overall mortality in the China Clinical Trials Consortium validation cohort excluding the molecular test

|  | HR | 95% CI | LR test p-value |
| --- | --- | --- | --- |
| Age >65 | 1.18 | 0.94-1.49 | 0.1532 |
| Female Sex | 0.93 | 0.70-1.22 | 0.5917 |
| Never Smoker | 0.74 | 0.56-0.97 | 0.0260 |

TABLE 15-continued

Multivariate cox proportional hazards model for 5-year overall mortality in the China Clinical Trials Consortium validation cohort excluding the molecular test

|  | HR | 95% CI | LR test p-value |
| --- | --- | --- | --- |
| Histology§ |  |  |  |
| Large Cell Carcinoma | 1.79 | 0.89-3.63 | 0.1374 |
| Mixed | 1.15 | 0.75-1.77 | 0.5221 |
| NSCLC NOS | 0.77 | 0.36-1.63 | 0.4707 |
| Stage§§ | 1.48 | 1.38-1.58 | <0.0001 |

§Compared to Adenocarcinoma
§§Modeled as a continuous variable

TABLE 16

Tabulation of risk factors by risk category in the China Clinical Trials Consortium validation cohort

|  | Low-Risk | Intermediate-Risk | High-Risk | P value |
| --- | --- | --- | --- | --- |
| Number of Patients | 193 | 172 | 602 |  |
| Age at Resection | 57.6 (11.4)§ | 58.5 (10.7)§ | 58.5 (10.6)§ | 0.5529* |
| Sex |  |  |  |  |
| Male | 98 (50.8) | 86 (50.0) | 417 (69.3) | <0.0001 |
| Female | 95 (49.2) | 86 (50.0) | 185 (30.7) |  |
| Smoking History |  |  |  |  |
| Yes | 70 (38.3) | 68 (43.9) | 354 (63.6) | <0.0001 |
| No | 113 (61.7) | 87 (56.1) | 203 (36.4) |  |
| Histology |  |  |  |  |
| Adenocarcinoma | 186 (96.4) | 159 (92.4) | 536 (89.0) | 0.0032 |
| Large Cell | 0 | 4 (2.3) | 13 (2.2) |  |
| Mixed | 4 (2.1) | 3 (1.7) | 43 (7.1) |  |
| NSCLC NOS | 3 (1.6) | 6 (3.5) | 10 (1.7) |  |
| Tumor Size (cm) | 2.8 (1.4)§ | 3.4 (1.7)§ | 4.3 (4.1)§ | <0.0001* |
| Stage |  |  |  |  |
| I | 130 (68.4) | 95 (55.6) | 246 (41.1) |  |
| II | 34 (17.9) | 32 (18.7) | 156 (26.1) | <0.0001 |
| III | 26 (13.7) | 44 (25.7) | 196 (32.8) |  |

Numbers in paratheses represent the percentage of patients in each risk category except where stated.
§Cohort Mean (Standard Deviation)
*ANOVA test In addition to multivariate analysis, a time-dependent AUROC analysis was performed to test whether the molecular assay provided more useful prognostic information than conventional staging alone. The AUROC is a measure of the discrimination of a prognostic test and coincides with the c-statistic. NCCN criteria, which identify such patients as stage IB plus at least one of the following risk factors, were used: poorly differentiated tumors, vascular invasion, wedge resection, minimal margins, tumors greater than 4 cm in diameter, visceral pleural involvement, and unknown lymph node status. The addition of the molecular assay gave better risk discrimination than did NCCN risk criteria alone in the Kaiser Permanente validation cohort, shown by a larger AUROC (c-statistic of 0.60 vs. 0.54; p<0.0001). Complete data were not available for all NCCN high-risk stage I criteria in patients from the CCTC cohort. AUROC analysis in this cohort therefore focused on 471 patients with stage I disease; addition of the molecular assay to conventional staging alone similarly increased the AUROC for this group, consistent with better discrimination in risk prediction by the addition of the molecular assay (c-statistic of 0.61 vs. 0.56; p<0.0001).

Discussion

The quantitative-PCR-based assay used in this Example was observed to reliably identify patients with early-stage non-squamous NSCLC at high risk for mortality after surgical resection, discriminating such patients with greater accuracy than use of NCCN criteria alone. This Example demonstrates the implemental of a platform with extraction of interpretable RNA from formalin-fixed paraffin-embedded tissue, the performance of the assay in one of the studies in a laboratory that was independent from the laboratory in which the assay was developed, the very large sizes of the independent validation cohorts, and the potentially large disparity between the genetic background of one of the validation cohorts and that of the original training cohort used for development of the assay.

The molecular assay used in this Example provides a more precise test for the definition of subsets of patients with non-squamous NSCLC and statistically heterogeneous outcomes. This assay was independently validated in a large, community-based American cohort to improve risk-stratification in patients with stage I disease. In view of the enormity of the public health crisis due to lung cancer in China, the additional validation of this molecular assay in a large Chinese population further increases its potential effect. This assay provides prognostic differentiation of patients with early-stage disease and might be helpful in the identification of the most appropriate application of treatment guidelines to improve clinical outcomes.

Example 3

AUROC Comparison for 11-Gene Assay Versus Other Assays with Different Gene Combinations This Example predicts the success of the 11-gene assay compared to other gene combinations in assigning patients to high or low risk categories using area under the receiver operating characteristic (AUROC) analysis.

AUROC analysis was performed on RNA samples extracted from 337 patients with stage I-IV lung cancer. As seen in Table 17 below, the 11-gene assay was observed to be superior to the other gene combinations tested in this Example, as reflected by a higher AUROC c-statistic.

TABLE 17

AUROC values

| Gene set | AUROC |
| --- | --- |
| BAG1 BRCA1 CDC6 CDK2AP1 ERBB3 FUT3 IL11 LCK RND3 SH3BGR WNT3A | 0.7215 |
| BAG1 BRCA1 CDC6 CDK2AP1 ERBB3 IL11 LCK | 0.6321 |
| BAG1 BRCA1 CDC6 RND3 | 0.5889 |
| BAG1 BRCA1 CDC6 FUT3 IL11 RND3 SH3BGR | 0.6438 |
| BAG1 BRCA1 CDC6 CDK2AP1 FUT3 IL11 RND3 SH3BGR | 0.6466 |
| BAG1 BRCA1 CDC6 CDK2AP1 EMX2 FUT3 IL11 LCK RND3 SH3BGR SIX3 | 0.6758 |
| BAG1 BRCA1 CDC6 CDK2AP1 ERBB3 IL11 RND3 SH3BGR | 0.6489 |
| BAG1 BRCA1 CDC6 CDK2AP1 EMX2 FUT3 IL11 RND3 SH3BGR SIX3 WNT3A | 0.6829 |
| BAG1 BRCA1 CDC6 CDK2AP1 EMX2 ERBB3 FUT3 IL11 LCK RND3 SIX3 | 0.6658 |
| BAG1 BRCA1 CDC6 CDK2AP1 ERBB3 FUT3 IL11 RND3 | 0.6382 |
| BAG1 BRCA1 CDC6 CDK2AP1 FUT3 IL11 LCK RND3 SH3BGR | 0.6767 |
| BAG1 BRCA1 CDC6 | 0.6280 |
| BAG1 BRCA1 CDC6 CDK2AP1 FUT3 IL11 RND3 | 0.6321 |
| BAG1 BRCA1 CDC6 CDK2AP1 ERBB3 FUT3 IL11 RND3 SH3BGR | 0.6531 |
| BAG1 BRCA1 CDC6 CDK2AP1 ERBB3 FUT3 IL11 LCK RND3 SH3BGR | 0.6815 |
| BAG1 BRCA1 CDC6 CDK2AP1 FUT3 IL11 WNT3A | 0.6735 |
| BAG1 BRCA1 CDC6 CDK2AP1 EMX2 ERBB3 FUT3 IL11 LCK RND3 SH3BGR SIX3 WNT3A | 0.6413 |
| CDK2AP1 FUT3 IL11 RND3 | 0.6276 |
| BAG1 BRCA1 CDC6 CDK2AP1 EMX2 ERBB3 FUT3 IL11 LCK RND3 SH3BGR SIX3 | 0.6823 |
| FUT3 IL11 RND3 | 0.5883 |
| BAG1 CDC6 FUT3 IL11 WNT3A | 0.6770 |
| BAG1 BRCA1 CDC6 FUT3 RND3 | 0.6298 |
| BAG1 BRCA1 CDC6 FUT3 IL11 RND3 SH3BGR | 0.6438 |
| BAG1 BRCA1 CDC6 CDK2AP1 ERBB3 IL11 RND3 | 0.6321 |
| BAG1 BRCA1 CDC6 CDK2AP1 EMX2 ERBB3 FUT3 IL11 RND3 SH3BGR SIX3 WNT3A | 0.6841 |
| BAG1 BRCA1 CDC6 CDK2AP1 ERBB3 FUT3 IL11 RND3 WNT3A | 0.6704 |
| BAG1 BRCA1 CDC6 CDK2AP1 ERBB3 FUT3 IL11 RND3 SH3BGR WNT3A | 0.6842 |
| ERBB3 LCK RND3 WNT3A | 0.6861 |
| ERBB3 LCK RND3 | 0.5821 |
| BAG1 CDC6 FUT3 IL11 RND3 | 0.6379 |

Gene Risk Property Selection

The 11-gene assay was analyzed to determine which genes conferred risk and which genes conferred protection using Cox Proportional Hazards Modeling. These determinations for each gene are listed in Table 18.

TABLE 18

Gene risk property of 11-gene assay

| Gene | Hazard Ratio | Property |
| --- | --- | --- |
| BAG1 | 1.002 | Risk |
| BRCA1 | 1.157 | Risk |
| CDC6 | 1.087 | Risk |
| CDK2AP1 | 1.205 | Risk |
| ERBB3 | 0.936 | Protection |
| FUT3 | 1.035 | Risk |
| IL11 | 1.014 | Risk |
| LCK | 0.811 | Protection |
| RND3 | 1.093 | Risk |
| SH3BGR | 0.820 | Protection |
| WNT3A | 0.888 | Protection |

Gene Coefficient Selection

The expression values of 11 genes (BAG1, BRCA1, CDC6, CDK2AP1, ERBB3, FUT3, IL11, LCK, RND3, SH3BGR, and WNT3A) may be combined in an infinite number of ways to yield a single number that is representative of that patient's risk of mortality. Each of the gene expression values were weighted (as represented by a coefficient) to represent the gene's relative contribution to a patient's risk of mortality. The coefficients for each of the genes in the 11-gene assay are listed in Table 19 below.

TABLE 19

Coefficients for genes in 11-gene assay

| Gene | Coefficient | Property | Risk Score AUROC |
|---|---|---|---|
| BAG1 | −0.0024 | Risk | 0.7215 |
| BRCA1 | −0.1461 | Risk | |
| CDC6 | −0.0834 | Risk | |
| CDK2AP1 | −0.1865 | Risk | |
| ERBB3 | 0.0664 | Protection | |
| FUT3 | −0.0346 | Risk | |
| IL11 | −0.0138 | Risk | |
| LCK | 0.2099 | Protection | |
| RND3 | −0.0885 | Risk | |
| SH3BGR | 0.1982 | Protection | |
| WNT3A | 0.1186 | Protection | |

AUROC Analysis

The risk score AUROC for the 11-gene assay was measured on a cohort of specimens from 337 patients who had undergone resection of lung cancer by measuring their risk scores and comparing risk assignment to the patients' actual 5-year survival outcomes. The AUROC c-statistic, which utilized the coefficients in Table 19 above, was 0.7215. Based on AUROC analysis, the 11-gene assay was observed to outperform other models (listed with their AUROC c-statistics in Tables 20-29 below), in which different coefficients were used to weight the contributions of the 11 genes.

TABLE 20

Alternative Model #1

| Gene | Coefficient | Property | Risk Score AUROC |
|---|---|---|---|
| BAG1 | −0.4806 | Risk | 0.6755 |
| BRCA1 | −0.2392 | Risk | |
| CDC6 | −0.4906 | Risk | |
| CDK2AP1 | −0.0386 | Risk | |
| ERBB3 | 0.4989 | Protection | |
| FUT3 | −0.3274 | Risk | |
| IL11 | −0.2656 | Risk | |
| LCK | 0.4071 | Protection | |
| RND3 | −0.2710 | Risk | |
| SH3BGR | 0.1232 | Protection | |
| WNT3A | 0.3385 | Protection | |

TABLE 21

Model #2

| Gene | Coefficient | Property | Risk Score AUROC |
|---|---|---|---|
| BAG1 | −0.0718 | Risk | 0.6715 |
| BRCA1 | −0.1588 | Risk | |
| CDC6 | −0.4781 | Risk | |
| CDK2AP1 | −0.1202 | Risk | |
| ERBB3 | 0.2770 | Protection | |
| FUT3 | −0.2002 | Risk | |
| IL11 | −0.2237 | Risk | |

TABLE 21-continued

Model #2

| Gene | Coefficient | Property | Risk Score AUROC |
|---|---|---|---|
| LCK | 0.2451 | Protection | |
| RND3 | −0.4197 | Risk | |
| SH3BGR | 0.1902 | Protection | |
| WNT3A | 0.2869 | Protection | |

TABLE 22

Model #3

| Gene | Coefficient | Property | Risk Score AUROC |
|---|---|---|---|
| BAG1 | −0.1630 | Risk | 0.6751 |
| BRCA1 | −0.0783 | Risk | |
| CDC6 | −0.4656 | Risk | |
| CDK2AP1 | −0.2018 | Risk | |
| ERBB3 | 0.0551 | Protection | |
| FUT3 | −0.0729 | Risk | |
| IL11 | −0.1818 | Risk | |
| LCK | 0.0832 | Protection | |
| RND3 | −0.0685 | Risk | |
| SH3BGR | 0.2572 | Protection | |
| WNT3A | 0.2354 | Protection | |

TABLE 23

Model #4

| Gene | Coefficient | Property | Risk Score AUROC |
|---|---|---|---|
| BAG1 | −0.4308 | Risk | 0.6385 |
| BRCA1 | −0.1066 | Risk | |
| CDC6 | −0.2033 | Risk | |
| CDK2AP1 | −0.1515 | Risk | |
| ERBB3 | 0.2706 | Protection | |
| FUT3 | −0.4905 | Risk | |
| IL11 | −0.4776 | Risk | |
| LCK | 0.1602 | Protection | |
| RND3 | −0.2419 | Risk | |
| SH3BGR | 0.4835 | Protection | |
| WNT3A | 0.2145 | Protection | |

TABLE 24

Model #5

| Gene | Coefficient | Property | Risk Score AUROC |
|---|---|---|---|
| BAG1 | −0.0220 | Risk | 0.6419 |
| BRCA1 | −0.0262 | Risk | |
| CDC6 | −0.1908 | Risk | |
| CDK2AP1 | −0.2331 | Risk | |
| ERBB3 | 0.0487 | Protection | |
| FUT3 | −0.3632 | Risk | |
| IL11 | −0.4358 | Risk | |
| LCK | 0.4983 | Protection | |
| RND3 | −0.3906 | Risk | |
| SH3BGR | 0.0506 | Protection | |
| WNT3A | 0.1630 | Protection | |

TABLE 25

Model #6

| Gene | Coefficient | Property | Risk Score AUROC |
|---|---|---|---|
| BAG1 | −0.0690 | Risk | 0.6652 |
| BRCA1 | −0.0436 | Risk | |
| CDC6 | −0.1157 | Risk | |
| CDK2AP1 | −0.2227 | Risk | |
| ERBB3 | 0.2175 | Protection | |
| FUT3 | −0.0998 | Risk | |
| IL11 | −0.1845 | Risk | |
| LCK | 0.0266 | Protection | |
| RND3 | −0.2833 | Risk | |
| SH3BGR | 0.4528 | Protection | |
| WNT3A | 0.3538 | Protection | |

TABLE 26

Model #7

| Gene | Coefficient | Property | Risk Score AUROC |
|---|---|---|---|
| BAG1 | −0.1602 | Risk | 0.6787 |
| BRCA1 | −0.4631 | Risk | |
| CDC6 | −0.1032 | Risk | |
| CDK2AP1 | −0.3042 | Risk | |
| ERBB3 | 0.4957 | Protection | |
| FUT3 | −0.4726 | Risk | |
| IL11 | −0.1426 | Risk | |
| LCK | 0.3646 | Protection | |
| RND3 | −0.4320 | Risk | |
| SH3BGR | 0.0198 | Protection | |
| WNT3A | 0.3023 | Protection | |

TABLE 27

Model #8

| Gene | Coefficient | Property | Risk Score AUROC |
|---|---|---|---|
| BAG1 | −0.2513 | Risk | 0.6882 |
| BRCA1 | −0.3827 | Risk | |
| CDC6 | −0.0907 | Risk | |
| CDK2AP1 | −0.3858 | Risk | |
| ERBB3 | 0.2738 | Protection | |
| FUT3 | −0.3453 | Risk | |
| IL11 | −0.1007 | Risk | |
| LCK | 0.2027 | Protection | |
| RND3 | −0.0808 | Risk | |
| SH3BGR | 0.0869 | Protection | |
| WNT3A | 0.2507 | Protection | |

TABLE 28

Model #9

| Gene | Coefficient | Property | Risk Score AUROC |
|---|---|---|---|
| BAG1 | −0.3425 | Risk | 0.6717 |
| BRCA1 | −0.3023 | Risk | |
| CDC6 | −0.0782 | Risk | |
| CDK2AP1 | −0.4674 | Risk | |
| ERBB3 | 0.0519 | Protection | |
| FUT3 | −0.2181 | Risk | |
| IL11 | −0.0588 | Risk | |
| LCK | 0.0407 | Protection | |
| RND3 | −0.2296 | Risk | |
| SH3BGR | 0.1539 | Protection | |
| WNT3A | 0.1992 | Protection | |

TABLE 29

Model #10

| Gene | Coefficient | Property | Risk Score AUROC |
|---|---|---|---|
| BAG1 | −0.4336 | 0.3686239 | 0.6797 |
| BRCA1 | −0.2218 | Risk | |
| CDC6 | −0.0657 | Risk | |
| CDK2AP1 | −0.0490 | Risk | |
| ERBB3 | 0.3301 | Protection | |
| FUT3 | −0.0909 | Risk | |
| IL11 | −0.0169 | Risk | |
| LCK | 0.3788 | Protection | |
| RND3 | −0.3783 | Risk | |
| SH3BGR | 0.2209 | Protection | |
| WNT3A | 0.1477 | Protection | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a subject having stage I non-small cell lung cancer (NSCLC), based on a prognosis, the method comprising the steps of:
   (a) contacting a biological sample from the subject with assay reagents that specifically bind to at least eleven biomarkers, wherein the eleven biomarkers consist of BAG1, BRCA1, CDC6, CDK2AP1, ERBB3, FUT3, IL11, LCK, RND3, SH3BGR, and WNT3A;
   (b) determining the levels of mRNA expression of the biomarkers in the sample using a quantitative PCR assay;
   (c) determining a risk score of the subject based on the levels of mRNA expression of the biomarkers in the sample;
   (d) using the risk score to provide a prognosis for the subject, wherein the risk score is indicative of said prognosis, and wherein the prognosis provides a low risk assessment or a high risk assessment; and
   (e) treating the subject having a high risk assessment with adjuvant chemotherapy.

2. The method of claim 1, wherein the expression of BAG1, BRCA1, CDC6, CDK2AP1, FUT3, IL11, and RND3 indicate an increased likelihood in mortality of the subject, and wherein the expression of ERBB3, LCK, SH3BGR, and WNT3A indicate a decreased likelihood in mortality of the subject.

3. The method of claim 1, wherein the reagents are nucleic acids.

4. The method of claim 1, wherein the reagents are oligonucleotides.

5. The method of claim 1, wherein the reagents are PCR primer sets.

6. The method of claim 1, wherein the sample is from a surgically resected tumor.

7. The method of claim 1, wherein the sample is from lung tissue or a lung tumor biopsy.

8. The method of claim 1, wherein the determining of a risk score of the subject based on the levels of expression of the biomarkers in the sample further comprises normalizing the levels of expression of the biomarkers to housekeeping genes selected from the group consisting of ESD, TBP, YAP1, and any combinations thereof.

9. The method of claim 1, wherein the levels of expression of the biomarkers are normalized against the average $C_T$ value of the housekeeping genes.

10. The method of claim 1, wherein the assay reagents are designed to target a 65-85 base pair region of the mRNA of each biomarker, and wherein the 65-85 base pair region of the mRNA of each biomarker crosses an exon-exon boundary.

11. The method of claim 1, wherein the prognosis provides a high risk assessment for mortality.

12. The method of claim 11, wherein the prognosis provides a high risk assessment for 5-year mortality.

13. The method of claim 1, wherein the prognosis provides a low risk assessment for mortality.

14. The method of claim 13, wherein the prognosis provides a low risk assessment for 5-year mortality.

15. The method of claim 1, wherein the prognosis provides a high risk assessment for recurrence.

16. The method of claim 1, wherein the prognosis provides a low risk assessment for recurrence.

17. A method of treating a subject having stage I non-small cell lung cancer (NSCLC), based on a prognosis, the method comprising the steps of:
  (a) contacting a biological sample from the subject with assay reagents that specifically bind to at least eleven biomarkers, wherein the eleven biomarkers consist of BAG1, BRCA1, CDC6, CDK2AP1, ERBB3, FUT3, IL11, LCK, RND3, SH3BGR, and WNT3A;
  (b) determining the levels of mRNA expression of the biomarkers in the sample using a quantitative PCR assay;
  (c) determining a risk score of the subject based on the levels of mRNA expression of the biomarkers in the sample;
  (d) using the risk score to provide a prognosis for the subject, wherein the risk score is indicative of said prognosis, and wherein the prognosis provides a low risk assessment, an intermediate risk assessment, or a high risk assessment; and
  (e) treating the subject having a high risk assessment with adjuvant chemotherapy.

18. The method of claim 17 further comprising treating the subject having an intermediate risk assessment with adjuvant chemotherapy.

19. The method of claim 17, wherein the determining of a risk score of the subject based on the levels of expression of the biomarkers in the sample further comprises normalizing the levels of expression of the biomarkers to housekeeping genes selected from the group consisting of ESD, TBP, YAP1, and any combinations thereof.

20. The method of claim 17, wherein the levels of expression of the biomarkers are normalized against the average $C_T$ value of the housekeeping genes.

21. The method of claim 17, wherein the expression of BAG1, BRCA1, CDC6, CDK2AP1, FUT3, IL11, and RND3 indicate an increased likelihood in mortality of the subject, and wherein the expression of ERBB3, LCK, SH3BGR, and WNT3A indicate a decreased likelihood in mortality of the subject.

22. The method of claim 17, wherein the reagents are nucleic acids.

23. The method of claim 17, wherein the reagents are oligonucleotides.

24. The method of claim 17, wherein the reagents are PCR primer sets.

25. The method of claim 17, wherein the sample is from a surgically resected tumor.

26. The method of claim 17, wherein the sample is from lung tissue or a lung tumor biopsy.

27. The method of claim 17, wherein the prognosis provides a high risk assessment for mortality.

28. The method of claim 27, wherein the prognosis provides a high risk assessment for 5-year mortality.

29. The method of claim 17, wherein the prognosis provides a low risk assessment for mortality.

30. The method of claim 29, wherein the prognosis provides a low risk assessment for 5-year mortality.

31. The method of claim 17, wherein the prognosis provides an intermediate risk assessment for mortality.

32. The method of claim 31, wherein the prognosis provides an intermediate risk assessment for 5-year mortality.

33. The method of claim 17, wherein the prognosis provides a high risk assessment for recurrence.

34. The method of claim 17, wherein the prognosis provides a low risk assessment for recurrence.

35. The method of claim 17, wherein the prognosis provides an intermediate risk assessment for recurrence.

* * * * *